(12) United States Patent
Ellis-Behnke et al.

(10) Patent No.: US 9,084,752 B2
(45) Date of Patent: Jul. 21, 2015

(54) COMPOSITIONS AND METHODS FOR CONTROLLING PROLIFERATION AND DIFFERENTIATION OF CELLS

(75) Inventors: Rutledge Ellis-Behnke, Myrtle Beach, SC (US); David Kiong-Chiu Tay, Hong Kong (HK)

(73) Assignee: The University of Hong Kong, Hong Kong (HK)

( * ) Notice: Subject to any disclaimer, the term of this patent is extended or adjusted under 35 U.S.C. 154(b) by 721 days.

(21) Appl. No.: 12/966,612

(22) Filed: Dec. 13, 2010

(65) Prior Publication Data

US 2011/0150844 A1    Jun. 23, 2011

Related U.S. Application Data

(60) Provisional application No. 61/286,363, filed on Dec. 14, 2009.

(51) Int. Cl.
*A61K 38/10* (2006.01)
*A61K 35/12* (2006.01)
*C12N 5/00* (2006.01)

(52) U.S. Cl.
CPC .............. *A61K 38/10* (2013.01); *C12N 5/0068* (2013.01); *A61K 35/12* (2013.01); *C12N 2533/50* (2013.01)

(58) Field of Classification Search
CPC ................................ A61K 38/10; A61K 35/12
See application file for complete search history.

(56) References Cited

U.S. PATENT DOCUMENTS

| | | | |
|---|---|---|---|
| 5,670,483 A | 9/1997 | Zhang | |
| 5,955,343 A | 9/1999 | Holmes | |
| 6,548,630 B1 | 4/2003 | Zhang | |
| 6,800,481 B1 | 10/2004 | Holmes | |
| 7,399,831 B2 * | 7/2008 | Lee et al. | 530/350 |
| 7,449,180 B2 * | 11/2008 | Kisiday et al. | 424/93.7 |
| 2005/0287186 A1 | 12/2005 | Ellis-Behnke | |
| 2008/0274979 A1 | 11/2008 | Ellis-Behnke | |

FOREIGN PATENT DOCUMENTS

WO    WO 02/062969    * 8/2002 ............... C12N 5/00

OTHER PUBLICATIONS

Caplan, et al., "Self-assembly of a beta-sheet protein governed by relief of electrostatic repulsion relative to van der Waals attraction", Biomacromolecules, 1:627-631 (2000).
Caplan, et al., "Control of self-assembling oligopeptide matrix formation through systematic variation of amino acid sequence", Biomaterials, 23:219-227 (2002).
Ellis-Behnke, et al., "Using nanotechnology to design potential therapies for CNS regeneration", Curr. Pharm. Des., 13:2519-2528 (2007).
Ellis-Behnke, et al., "Nano neuro knitting: peptide nanofiber scaffold for brain repair and axon regeneration with functional return of vision", PNAS, 103:5054-5059 (2006).
Guo, et al., "Reknitting the injured spinal cord by self-assembling peptide nanofiber scaffold", Neurology Nanomedicine, 3:311-321 (2007).
Holmes, et al., "Extensive neurite outgrowth and active synapse formation on self-assembling peptide scaffolds", PNAS, 97:6728-6733 (2000).
Kendhale et al., "Isotactic N-alkyl acrylamide oligomers assume self-assembled sheet structure: first unequivocal evidence from crystal structures", Chem Comm, 14:2756-58, (2006).
Leach, et al., "Neurite outgrowth and branching of PC12 cells on very soft substrates sharply decreases below a threshold of substrate rigidity", J. Neural Eng., 4:26-34 (2007).
Leon et al., "Mechanical properties of a self-assembling oligopeptide matrix", J. Biomater. Sci. Polym. Ed., 9:297-312 (1998).
Ma, et al., "Supramolecular polymer chemistry: self-assembling dendrimers using the DDA.AAD (GC-like) hydrogen bonding motif", J. Am. Chem. Soc., 124(46), 13757-13769 (2002).
Moore, et al., "A field guide to foldamers", Chem. Rev. 101(12):3893-4012 (2001).
Pelham and Wang, "Cell locomotion and focal adhesions are regulated by substrate flexibility", PNAS., 94:13661-13665 (1997).
Schmidt and Leach, "Neural tissue engineering: strategies for repair and regeneration", Ann. Rev. Eng., 5:293-347 (2003).
Takenaga, et al., "Plasma as a scaffold for regeneration of neural precursor cells after transplantation into rats with spinal cord injury", Cell Transplant., 16:57-65 (2007).
Willerth and Sakiyama-Elbert, "Cell therapy for spinal cord regeneration", Adv. Drug. Deily. Rev., 60:263-276 (2008).
Zhang et al., "Self-complementary oligopeptide matrices support mammalian cell attachment", Biomaterials, 16:1385-1393 (1995).
Zhang, et al., "Spontaneous assembly of a self-complementary oligopeptide to form a stable macroscopic membrane", PNAS, 90:3334-3338 (1993).
Zhang, "Fabrication of novel biomaterials through molecular self-assembly", Nat. Biotechnol., 21:1171-1178 (2003).
Zimmerman, et al., "Self-assembling dendrimers", Science, 271(5252)1095-98 (1996).

* cited by examiner

*Primary Examiner* — Amber D Steele
(74) *Attorney, Agent, or Firm* — Pabst Patent Group LLP

(57) ABSTRACT

Methods and compositions for modulating cell differentiation, proliferation and morphology in vitro or in vivo are described. The methods include modifying the extracellular nanoenvironment of stem cells with a self-assembling peptide nanofiber scaffold. The extracellular nanoenvironment can be modified by changing the percentage of self-assembling peptides used to form the nanofiber scaffold, the concentration of cells in the nanofiber scaffold, the pH, or the amounts of serum. Modulating the extracellular nanoenvironment of cells in nanofiber scaffold allows for increased targeting of cell placement and therapeutic delivery, amplified by cell encapsulation and implantation.

22 Claims, 3 Drawing Sheets

COMPOSITIONS AND METHODS FOR CONTROLLING PROLIFERATION AND DIFFERENTIATION OF CELLS

CROSS REFERENCE TO RELATED APPLICATIONS

This application claims benefit of U.S. Provisional Application No. 61/286,363, filed Dec. 14, 2009, which is hereby incorporated herein by reference in its entirety.

REFERENCE TO SEQUENCE LISTING

The Sequence Listing submitted Dec. 12, 2013 as a text file named "UHK_00328_ST25.txt," created on Nov. 12, 2013, and having a size of 1,064 bytes is hereby incorporated by reference pursuant to 37 C.F.R. §1.52(e)(5).

FIELD OF THE INVENTION

The invention is generally related to compositions that modulate the proliferation, differentiation and morphology of cells, and methods of use in areas including tissue regeneration and wound repair.

BACKGROUND OF THE INVENTION

Regenerative medical technologies include methods that repair or replace diseased or defective tissues or organs. Tissue engineering is the application of the principles and methods of engineering and the life sciences to the development of biological substitutes to restore, maintain or improve function of bodily structures and tissues, or to selectively promote the destruction of undesired tissues. It involves the development of methods to build biological substitutes as supplements or alternatives to whole organ or tissue transplantation, or the development of strategies to manipulate tissues in vivo. The use of living cells and/or extracellular matrix (ECM) components in the development of implantable parts or devices is an attractive approach to restore or to replace function.

The advent of nanotechnology has ushered in a new era of tissue and organ reconstruction. Fine control of the extracellular nanoenvironment allows for increased targeting of cell placement and therapeutic delivery, amplified by cell encapsulation and implantation. Small changes in the cellular environment can lead to the activation of the apoptotic pathway or even necrosis of the cells weeks after implantation. The successful storage and implantation of stem cells pose significant challenges for tissue engineering in the nervous system, in addition to the challenges inherent to neural regeneration e.g., formation of the glial scar that surrounds the lesions caused by traumatic brain injury (TBI) or stroke, and the cystic cavities in spinal cord injury (SCI) (Fawcett and Asher, *Brain Res. Bull.*, 49:377-391 (1999)).

Scaffolds play a central role in organ regeneration (Ellis-Behnke, et al., *Curr. Pharm. Des.*, 13:2519-2528 (2007)). They act as a template and guide for cell proliferation, cell differentiation and tissue growth, as well as control the release of drugs at rates matching the physiological need of the tissue (Langer, *Nature*, 392 (Supp):5-10 (1998)). The surface of the scaffold provides a substrate for cell adhesion and migration, which can influence the survival of transplanted cells or the invasion of cells from the surrounding tissue. Although many promising strategies have been developed for controlling the release of drugs from scaffolds, there are still challenges to be addressed for these scaffolds to serve as successful treatments (Holmes, et al., *Proc. Natl. Acad. Sci. USA.*, 97:6728-6733 (2000); Schmidt and Leach, *Ann. Rev. Eng.*, 5:295-347 (2003); Willerth and Sakiyama-Elbert, *Adv. Drug. Deliv. Rev.*, 60:263-276 (2008); Zhang, et al., *Biomaterials*, 16:1385-1393 (1995); Zhang, et al., *Proc. Natl. Acad. Sci. USA*, 90:3334-3338 (1993)). For example, the precise placement of the cells into the scaffold must be addressed to prevent migration of the cells from the scaffold before it has been repopulated. Additionally, the ability of the scaffold to allow cells to migrate into it, in order to reconstitute the tissue from the surrounding area, must be addressed. Lastly, the prevention of the acidic breakdown of the cell scaffold, which results in an adverse environment for cell growth, remains problematic. Many types of scaffolds, utilizing a wide range of materials, have been used for the regeneration and repair of the nervous system (Takenaga, et al., *Cell Transplant.*, 16:57-65 (2007); Zhang, *Nat. Biotechnol.*, 21:1171-1178 (2003)). In treating TBI or SCI, drug delivering scaffolds may need to be combined with cell transplantation to obtain functional recovery (Willerth and Sakiyama-Elbert, *Adv. Drug Deliv. Res.*, 60-263-276 (2008)).

To successfully reconstruct tissues and organs, cellular therapies must integrate into the injury site. For central nervous system (CNS) injuries, regeneration is not just replacement but regrowth of the lost neuronal circuitry, followed by promotion of plasticity of the spared and regenerated neurons (Ellis-Behnke, et al., *Proc. Nat. Acad. Sci. USA*, 103:5054-5059 (2006); Willerth and Sakiyama-Elbert, *Adv. Drug Deliv. Res.*, 60-263-276 (2008)). PC12 cells change branching patterns and process densities depending on the modulus of the scaffold. If the modulus is less than 10 pascals (Pa), branching decreases along with neurite density, whereas when the modulus is between 100 Pa to 1000 Pa branching is more pronounced and the cells exhibit process outgrowth that is longer, with more cells expressing neurite markers (Leach, et al., *J. Neural Eng.*, 4:26-34 (2007); Pelham and Wang, *Proc. Natl. Acad. Sci. USA*, 94:13661-13665 (1997)). Other issues associated with human embryonic stem cell lines include the use of culture systems that rely on serum or feeder cell layers. There is a need for the development of culture methods for human stem cells that involve chemically defined media (Willerth and Sakiyama-Elbert, *Adv. Drug Deliv. Res.*, 60-263-276 (2008)). The end goal for cellular therapies is to create cell lines for transplantation that do not require immune suppression of the patient (Willerth and Sakiyama-Elbert, *Adv. Drug Deliv. Res.*, 60-263-276 (2008)).

Therefore, it is an object of the invention to provide compositions and methods that generate functional biological structure de novo or regenerate organs in situ, as well as to restore or supplement tissue function.

It is another objective to provide compositions and methods that modulate the differentiation, morphology and/or proliferation of cells, preferably stem cells.

SUMMARY OF THE INVENTION

Methods and compositions for modulating cell differentiation and proliferation in vitro or in vivo are described. The methods include modifying the extracellular nanoenvironment of the cells in a self-assembling peptide nanofiber scaffold. The extracellular nanoenvironment can be modified by changing the percentage of self-assembling peptides used to form the self-assembling peptide nanofiber scaffold, the concentration of cells in the self-assembling nanofiber scaffold, the pH, the presence of serum, or a combination thereof.

Modulating the extracellular nanoenvironment of cells in nanofiber scaffold allows for increased targeting of cell placement and therapeutic delivery, amplified by cell encapsulation and implantation.

In one embodiment, the self-assembling material comprises peptides having a sequence of amino acid residues conforming to one or more of Formulas I-IV:

$$((Xaa^{neu}-Xaa^+)_x(Xaa^{neu}-Xaa^-)_y)_n \quad (I)$$

$$((Xaa^{neu}-Xaa^-)_x(Xaa^{neu}-Xaa^+)_y)_n \quad (II)$$

$$((Xaa^+-Xaa^{neu})_x(Xaa^--Xaa^{neu})_y)_n \quad (III)$$

$$((Xaa^--Xaa^{neu})_x(Xaa^+-Xaa^{neu})_y)_n \quad (IV)$$

wherein $Xaa^{neu}$ represents an amino acid residue having a neutral charge; $Xaa^+$ represents an amino acid residue having a positive charge; $Xaa^-$ represents an amino acid residue having a negative charge; x and y are integers having a value of 1, 2, 3, or 4, independently; and n is an integer having a value of 1-5. In a preferred embodiment the self-assembling polypeptide has the amino acid sequence RADARADARADARADA (SEQ ID NO:1). In another embodiment the self-assembling polypeptide has the amino acid sequence RAEARAEARAEARAEA (SEQ ID NO:2).

The concentration of the self-assembling materials in any given formulation can vary and can be between approximately 0.01% and 99% wt/vol, inclusive, preferably between 0.01% and 10% wt/vol, or more preferably between 0.1 and 5% wt/vol. In some embodiments, the concentration of the self-assembling materials (e.g., in a liquid formulation) can be approximately 0.1-3.0% wt/vol (1-30 mg/ml). The concentration of self-assembling materials can be higher in stock solutions and in solid (e.g., powdered) formulations. Solid preparations may have a concentration of self-assembling materials approaching 100% (e.g., the concentration of self-assembling materials can be 95, 96, 97, 98, 99% or more of the composition). Whether in liquid or solid form, the materials can be brought to the desired concentration prior to use by addition of a pharmaceutically acceptable diluent. The formulations may include a pharmaceutically acceptable carrier or therapeutic, prophylactic or diagnostic agents. These include, but are not limited to, anti-inflammatories, vasoactive agents, anti-infectives, anesthetics, growth factors, and/or cells. Metals may be added as chelators or to further decrease adhesion.

The concentration of cells can also be modified to alter the extracellular nanoenvironment of the cells when they are in the scaffold. The cells are preferably stem cells, totipotent cells, pluripotent cells, multipotent cells, or combinations thereof. Differentiated cells can optionally be combined with the stem cells.

In some embodiments, at least 1,000 to 100,000 cells/μl, including about 1,000 to 30,000 cells/μl, 1,000 to 20,000 cells/μl, 1,000 to 10,000 cells/μl, and 5,000 to 20,000 cells/μl can be used. Therefore, the concentration of cells can be about 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000 cells/μl.

Another embodiment provides a composition for repairing tissue by administering to the tissue self-assembling peptides in combination with one or more stem cells, wherein the self-assembling peptides are present in an effective amount to form a self-assembling peptide scaffold (three-dimensional matrix) to inhibit or reduce differentiation of the stem cells. For example, the tissue to be repaired can be neural tissue, cardiac tissue, muscle tissue, cartilage, arterial tissue, or bone.

The self-assembling peptide scaffolds can be used to inhibit or reduce cell differentiation by combining stem cells with an effective amount of self-assembling peptides to provide a three-dimensional matrix to inhibit or reduce cell differentiation. The self-assembling peptides can be assembled into a scaffold in vitro or in vivo. The cells can then be added to the assembled scaffold. Alternatively, the self-assembling peptides and cells can be combined and applied to a site in a subject where the self-assembling peptides assemble into a scaffold. The cells can then enter the scaffold, or the cells can be encapsulated as the scaffold forms. In another embodiment, the scaffold can be assembled in vitro. Cells are then added to the assembled scaffold and the combination of cells and scaffold are administered to a subject in need of tissue repair, augmentation, growth or a combination thereof.

The formulation may be applied as a hydrogel. In one embodiment, the formulation is applied as an injection or a hydrogel including a material such as chitin, collagen, alginate, or synthetic polymer. In some embodiments, the formulation is provided in a bandage, foam or matrix, in which the materials may be dispersed or absorbed. The formulation could also be in the form of sutures, tape, or adhesive. The liquid formulations may be provided in a syringe or pipette having a barrel containing a composition including self-assembling materials and a means for expelling the composition from an open tip of the syringe or pipette (e.g., a plunger or bulb). The syringe may include of one or more compartments, so that mixing of the self-assembling materials containing cells with one or more other agents occurs at the time of application. The compartments may also contain excipients such as a material forming a hydrogel or adhesive in one compartment and the self-assembling materials in the other compartment. In another embodiment, one compartment may contain lyophilized or particles of self-assembling materials, and another compartment may contain solution to dissolve or hydrate the materials, or mixed with other powders for dry application.

One or more of the compositions described herein can be assembled in kits, together with instructions for use. For example, the kits can include a biocompatible composition including self-assembling materials (or a concentrated solution or powdered formulation thereof, together with a diluent) and instructions for their combination with stem cells, storage, and administration. The kits can include a vasoconstrictor, a coloring agent, or an analgesic or anesthetic agent and instructions for their combination (if not already combined) and use (e.g., dilution and administration). The kits can further include one or more of the additional agents described herein. These agents can be present within the self-assembling composition or packaged separately, and they can include one or more additional types of biological cells, an antibiotic or other therapeutic, collagen, an anti-inflammatory agent, a growth factor, or a nutrient. The kit may also include one or more of a syringe (e.g., a barrel syringe or a bulb syringe), a needle, a pipette, gauze, sponges, cotton, swabs, a bandage, a disinfectant, surgical thread, scissors, a scalpel, a sterile fluid, a spray canister, including those in which a liquid solution is sprayed through a simple hand pump, a sterile container, or disposable gloves. The kit may also include one or more additives to vary the assembly kinetics of the material depending on the environment in which the material is to be used.

DETAILED DESCRIPTION OF THE INVENTION

I. Definitions

Figure 1:
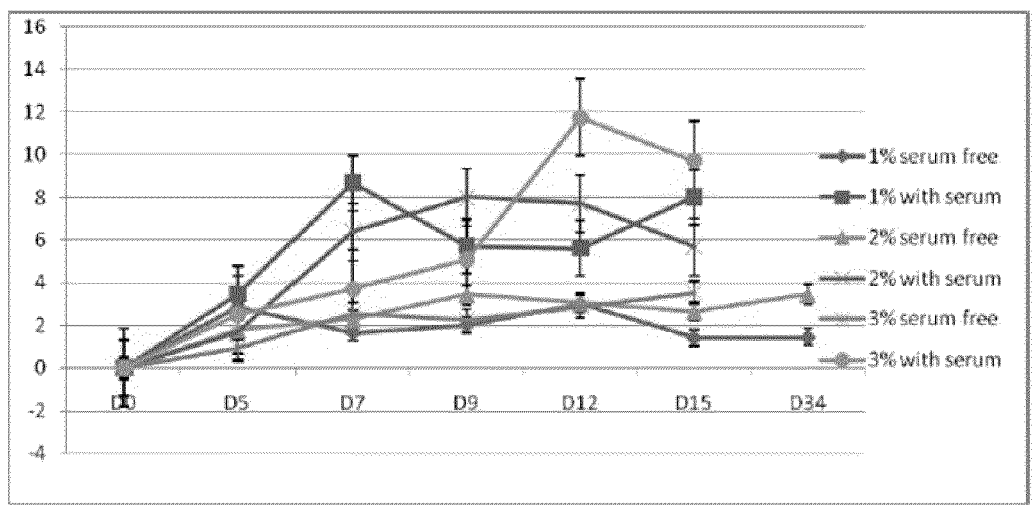
FIG. 1 is a line graph illustrating the number of processes per neural precursor cell (NPC) verses time (days). Closed diamonds represent 1% SAPNS, in serum free media. Closed squares represent 1% SAPNS, in media with serum. Closed triangles represent 2% SAPNS, in serum free media. "X"s represent 1% SAPNS, in media with serum. "Asterisks/stars" represent 3% SAPNS, in serum free media. Closed circles represent 3% SAPNS, with serum. Error bars=standard error.

The term "cell" or "cells" refers to fundamental unit of biological structure.

The term "stem cell" and "undifferentiated cell" are used interchangeably to refer to an unspecialized cell from an embryo, fetus, or adult that is capable of self-replication or self-renewal and can develop into specialized cell types of a variety of tissues and organs. Unless further specified, the term encompasses totipotent cells (those cells having the capacity to differentiate into extra-embryonic membranes and tissues, the embryo, and all post-embryonic tissues and organs), pluripotent cells (those cells that can differentiate into cells derived from any of the three germ layers), multi-potent cells (those cells having the capacity to differentiate into a limited range of differentiated cell types, for example a hematopoietic cell), and progenitor cells (those cells having the capacity to differentiate along a single cell lineage).

The term "isolated" refers to a cell type (e.g., a stem cell) that is purified substantially free of other cell types or cellular material with which it naturally occurs.

The term "proliferation" refers to cell proliferation where one cell grows and divides to become two.

The term "differentiation" refers the process by which a less specialized cells become more specialized (i.e. totipotent to multipotent, and so forth).

The term "peptide," as used herein includes "polypeptide," "oligopeptide," and "protein," and refers to a chain of at least two α-amino acid residues linked together by covalent bonds (e.g., peptide bonds).

The term "self-assembling peptide" or "SAP" refers to peptides that can self-assemble into a nanofiber scaffold.

The term "SAPNS" is an acronym for self-assembling peptide nanofiber scaffold, and refers to self-assembling peptides that have self-assembled into two- or three-dimensional scaffolds.

The term "extracellular nanoenvironment" refers to the extracellular environment of a cell in a self-assembling peptide nanofiber scaffold on the nanometer, micro and macro] scale.

The term "biocompatible" refers to compatibility with living tissue or a living system by not being toxic, injurious, or physiologically reactive and not causing immunological rejection.

The term "complementary" refers to the capability of forming ionic or hydrogen bonding interactions between hydrophilic residues from adjacent peptides in a structure. Each hydrophilic reside in a peptide either hydrogen bonds or ionically pairs with a hydrophilic residue on an adjacent peptide, or is exposed to solvent. Pairing may also involve van der Waals forces.

The term "effective amount" refers to an active agent such as a self-assembling peptide or biomolecule, pharmaceutical agent, etc. refers to the amount necessary to elicit a desired biological response. As will be appreciated by those of ordinary skill in this art, the effective amount of an agent may vary depending on such factors as the desired biological endpoint, the agent to be delivered, the nature of the site to which the agent is delivered, the nature of the conditions for which the agent is administered, etc. For example, the effective amount of a composition for promoting tissue repair may be an amount sufficient to promote recovery to a greater extent than would occur in the absence of the composition.

The term "preventing" refers to causing a condition, state, or disease, or symptom or manifestation of such, or worsening of the severity of such, not to occur. Preventing includes reducing the risk that a condition, state, or disease, or symptom or manifestation of such, or worsening of the severity of such, will occur.

The term "repair", as used in reference to the repair of tissue in various embodiments of the invention, may include any aspect of anatomical or functional restoration of the condition of the tissue prior to an injury, deterioration, or other damage. For example, it may include restoration of physical continuity between portions of tissue that were separated by injury, deterioration, or other damage. Preferably such restoration of physical continuity includes reposition or reconnection of the portions of tissue without appreciable separation by tissue of a type that was not present prior to the injury, such as scar tissue. Repair may, but need not, include growth or development of new tissue. "Repair" and "Healing" are used interchangeably herein.

II. Compositions for Modulating Extracellular Nanoenvironment

Compositions and methods for modulating the extracellular nanoenvironment of cells to control differentiation and/or proliferation are described. The compositions include self-assembling materials (e.g. self-assembling peptides) and undifferentiated cells. The compositions can optionally include therapeutic and/or bioactive agents, media, and excipients. Typically, the composition of self-assembling materials and undifferentiated cells is administered to a wound, injury site, or location in a subject in need of tissue repair, augmentation, or regeneration.

Placing cells into a defined system on a 2-dimensional or within a 3-dimensional (3D) scaffold (e.g., nanofiber scaffold formed from self-assembling materials) provides a microenvironment for better control over growth and differentiation in order to effectively mimic the extracellular matrix both in vitro and in vivo. Cells can live and grow on or within (e.g. encapsulated within) nanofiber scaffold formed from self-assembling materials. Since the body does not treat the self-assembling material as a foreign material, it can be used to create microenvironment uniquely tailored to suit the selected method. The microenvironment can be manipulated to tune a variety of essential parameters. Proliferation, growth, differentiation, morphology, and migration potential of cells can be programmed by adjusting the concentration of self-assembling materials (e.g. self-assembling peptides). Proliferation, growth, differentiation, morphology, and migration potential of cells can also be programmed by the addition of additives such as serum, growth factors, and buffering agents. Once the system has been defined, the composition can be used for a variety of methods such as growing or storing cells in vitro, or repairing damaged or diseased tissue in vivo.

A. Self-Assembling Materials

1. Self-Assembling Peptides

Self-assembling materials are known in the art and are commercially available. In some embodiments, the self-assembling material is a self-assembling peptide (SAP). Suitable SAPs that can be used to modulate the extracellular nanoenvironment of undifferentiated cells are described in U.S. published application 2008/0274979 and U.S. Pat. Nos. 7,449,180; 5,670,483; 5,955,343; 6,548,630; and 6,800,481 to Zhang et al.; Holmes et al., *Proc. Natl. Acad. Sci. USA*, 97:6728-6733 (2000); Zhang et al., *Proc. Natl. Acad. Sci. USA*, 90:3334-3338 (1993); Zhang et al., *Biomaterials*, 16:1385-1393 (1995); Caplan et al., *Biomaterials*, 23:219-227 (2002); Leon et al., *J. Biomater. Sci. Polym. Ed.*, 9:297-312 (1998); and Caplan et al., *Biomacromolecules*, 1:627-631 (2000). One preferred SAP has the amino acid sequence RADARADARADARADA (RADA16-I, SEQ ID NO:1). Another embodiment has the amino acid sequence RAEARAEARAEARAEA (SEQ ID NO:2).

Useful peptides can vary in length so long as they retain the ability to self-assemble to an extent useful for one or more of the purposes described herein. The number of amino acid residues in the peptide may range from as few as two α-amino acid residues to about 200 residues. Typically, peptides which self-assemble have from about 6 to about 200 residues, preferably from about 6 to about 64 residues, more preferably from about 8 to about 36 residues, most preferably from about 8 to about 24 residues. The peptides can be at least six amino acids in length (e.g., eight or 10 amino acids), at least 12 amino acids in length (e.g., 12 or 14 amino acids), or at least 16 amino acids in length (e.g., 16, 18, 20, 22, or 24 amino acids). Peptides that are less than 100 amino acid residues long, more preferably less than approximately 50 amino acids in length, may assemble more readily. In one embodiment, the peptide has from about 8 to about 16 residues. In another embodiment, the peptide has from about 12 to about 20 residues. In yet another embodiment, the peptide has from about 16 to about 20 residues. "Peptide" may refer to an individual peptide or to a collection of peptides having the same or different sequences, any of which may contain naturally occurring α-amino acid residues, non-naturally occurring α-amino acid residues, and combinations thereof. α-Amino acid analogs are also known in the art and may alternatively be employed. In particular, D-α-amino acid residues may be used.

In addition, one or more of the amino acid residues in a self-assembling peptide can be altered or derivatized by the addition of one or more chemical entities including, but not limited to, acyl groups, carbohydrate groups, carbohydrate chains, phosphate groups, farnesyl groups, isofarnesyl groups, fatty acid groups, or a linker which allows for conjugation or functionalization of the peptide. For example, either or both ends of a given peptide can be modified. For example, the carboxyl and/or amino groups of the carboxyl- and amino-terminal residues, respectively can be protected or not protected. The charge at a terminus can also be modified. For example, a group or radical such as an acyl group (RCO—, where R is an organic group (e.g., an acetyl group ($CH_3CO$—)) can be present at the N-terminus of a peptide to neutralize an "extra" positive charge that may otherwise be present (e.g., a charge not resulting from the side chain of the N-terminal amino acid). Similarly, a group such as an amine group (RNH—, where R is an organic group (e.g., an amino group —$NH_2$)) can be used to neutralize an "extra" negative charge that may otherwise be present at the C-terminus (e.g., a charge not resulting from the side chain of the C-terminal amino acid residue). Where an amine is used, the C-terminus bears an amide (—CONHR). The neutralization of charges on a terminus may facilitate self-assembly. One of ordinary skill in the art will be able to select other suitable groups.

Useful peptides can also be branched, in which case they will contain at least two amino acid polymers, each of which consists of at least three amino acid residues joined by peptide bonds. The two amino acid polymers may be linked by a bond other than a peptide bond.

Self-assembling peptides can be chemically synthesized or purified from natural or recombinantly-produced sources by methods well known in the art. For example, peptides can be synthesized using standard f-moc chemistry and purified using high pressure liquid chromatography (HPLC).

While the sequences of the peptides can vary, useful sequences include those that convey an amphiphilic nature to the peptides (e.g., the peptides can contain approximately equal numbers of hydrophobic and hydrophilic amino acid residues), and the peptides can be complementary and structurally compatible. Complementary peptides have the ability to form ionic or hydrogen bonds between residues (e.g., hydrophilic residues) on adjacent peptides in a structure. For example, one or more hydrophilic residues in a peptide can either hydrogen bond or ionically pair with one or more hydrophilic residues on an adjacent peptide.

Where self-assembling peptides are used, it is thought that their side chains (or R groups) partition into two faces, a polar face with positively and/or negatively charged ionic side chains, and a nonpolar face with side chains that are considered neutral or uncharged at physiological pH (e.g., the side chain of an alanine residue or residues having other hydrophobic groups). The positively charged and negatively charged amino acid residues on the polar face of one peptide can form complementary ionic pairs with oppositely charged residues of another peptide. These peptides may therefore be called ionic, self-complementary peptides. If the ionic residues alternate with one positively and one negatively charged residue on the polar face (−+−+−+−+), the peptides may be described as "modulus I;" if the ionic residues alternate with two positively and two negatively charged residues (−−++−−++) on the polar face, the peptides are described as "modulus II;" if the ionic residues alternate with three positively and three negatively charged residues (+++−−−+++−−−) on the polar face, the peptides are describe as "modulus III;" if the ionic residues alternate with four positively and four negatively charged residues (++++−−−−++++−−−−) on the polar face, they are described as "modulus IV."

The self-assembling peptides can comprise a sequence of amino acid residues conforming to one or more of Formulas I-IV:

$$((Xaa^{neu}–Xaa^+)_x(Xaa^{neu}–Xaa^-)_y)_n \quad (I)$$

$$((Xaa^{neu}–Xaa^-)_x(Xaa^{neu}–Xaa^+)_y)_n \quad (II)$$

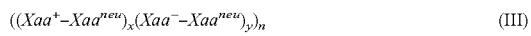

$$((Xaa^+\text{-}Xaa^{neu})_x(Xaa^-\text{-}Xaa^{neu})_y)_n \quad (III)$$

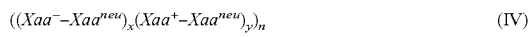

$$((Xaa^-\text{-}Xaa^{neu})_x(Xaa^+\text{-}Xaa^{neu})_y)_n \quad (IV)$$

Xaa$^{neu}$ represents an amino acid residue having a neutral charge; Xaa$^+$ represents an amino acid residue having a positive charge; Xaa$^-$ represents an amino acid residue having a negative charge; x and y are integers having a value of 1, 2, 3, or 4, independently; and n is an integer having a value of 1-5. Peptides with modulus I (i.e., peptides having alternate positively and negatively charged R groups on one side (e.g., the polar face of the β-sheet) are described by each of Formulas I-IV, where x and y are 1. Peptides of modulus II (i.e., peptides having two residues bearing one type of charge (e.g., a positive charge) followed by two residues bearing another type of charge (e.g., a negative charge)) are described by the same formulas where both x and y are 2. Examples of peptides of modulus III (i.e. peptides having three residues bearing one type of charge (e.g., a positive charge) followed by three residues bearing another type of charge (e.g., a negative charge)) include, but are not limited to, RARARARADADADADA (SEQ ID NO:3).

Other hydrophilic residues that form hydrogen bonds including, but not limited to, asparagine and glutamine, may be incorporated into the peptides. If the alanine residues in the peptides are changed to more hydrophobic residues, such as leucine, isoleucine, phenylalanine or tyrosine, the resulting peptides have a greater tendency to self-assemble and form peptide matrices with enhanced strength. Some peptides that have similar amino acids compositions and lengths as the peptides described here form alpha-helices and random-coils rather than beta-sheets and do not form macroscopic structures. Thus, in addition to self-complementarity, other factors are likely to be important for the formation of macroscopic structures, such as the peptide length, the degree of intermolecular interaction, and the ability to form staggered arrays.

Unpaired residues can interact (e.g. form hydrogen bonds, etc,) with the solvent. Peptide-peptide interactions may also involve van der Waals forces and/or forces that do not constitute covalent bonds. The peptides are structurally compatible when they are capable of maintaining a sufficiently constant intrapeptide distance to allow self-assembly and structure formation. The intrapeptide distance can vary. "Intrapeptide distance", as used herein, refers to the average of a representative number of distances between adjacent amino acid residues. In one embodiment, the intrapeptide distance is less than about 4 angstroms, preferably less than about 3, more preferably less than about 2 angstroms, and most preferably less than about 1 Angstrom. The intrapeptide distance may be larger than this, however. These distances can be calculated based on molecular modeling or based on a simplified procedure described in U.S. Pat. No. 5,670,483 to Zhang et al.

The structures described herein can be formed through self-assembly of the peptides described in U.S. Pat. Nos. 5,670,483; 5,955,343; 6,548,630; and 6,800,481 to Zhang et al.; Holmes et al., *Proc. Natl. Acad. Sci. USA*, 97:6728-6733 (2000); Zhang et al., *Proc. Natl. Acad. Sci. USA*, 90:3334-3338 (1993); Zhang et al., *Biomaterials*, 16:1385-1393 (1995); Caplan et al., *Biomaterials*, 23:219-227 (2002); Leon et al., *J. Biomater. Sci. Polym. Ed.*, 9:297-312 (1998); and Caplan et al., *Biomacromolecules*, 1:627-631 (2000).

Other peptides or proteins can be used in combination or alternation with the disclosed self-assembling peptides or compositions. It will be appreciated that the additional peptides can include other self-assembling peptides or proteins. Alternatively, the peptide may be peptides that do not self-assemble.

Other useful self-assembling peptides can be generated, for example, which differ from those exemplified by a single amino acid residue or by multiple amino acid residues (e.g., by inclusion or exclusion of a repeating quartet). For example, one or more cysteine residues may be incorporated into the peptides, and these residues may bond with one another through the formation of disulfide bonds. Structures bonded in this manner may have increased mechanical strength relative to structures made with comparable peptides that do not include cysteine residues and thus are unable to form disulfide bonds.

Self-assembled structures can be formed that have varying degrees of stiffness or elasticity. The structures typically have a low elastic modulus (e.g., a modulus in the range of 0.01-1000 kPa, preferably from 1-10 kPa as measured by standard methods, such as in a standard cone-plate rheometer). Low values may be preferable, as they permit structure deformation as a result of movement, in response to pressure, in the event of cell contraction. More specifically, stiffness can be controlled in a variety of ways, including by changing the length, sequence, and/or concentration of the precursor molecules (e.g., self-assembling peptides). Other methods for increasing stiffness can also be employed. For example, one can attach, to the precursors, biotin molecules or any other molecules that can be subsequently cross-linked or otherwise bonded to one another. The molecules (e.g., biotin) can be included at an N- or C-terminus of a peptide or attached to one or more residues between the termini. Where biotin is used, cross-linking can be achieved by subsequent addition of avidin. Biotin-containing peptides or peptides containing other cross-linkable molecules are representative of cross-linkable peptides. For example, amino acid residues with polymerizable groups, such as vinyl groups may be incorporated and cross-linked by exposure to UV light. The extent of crosslinking can be precisely controlled by applying the radiation for a predetermined length of time to peptides of known sequence and concentration. The extent of crosslinking can be determined by light scattering, gel filtration, or scanning electron microscopy using standard methods. Furthermore, crosslinking can be examined by HPLC or mass spectrometry analysis of the structure after digestion with a protease, such as matrix metalloproteases. Material strength may be determined before and after cross-linking Regardless of whether cross-linking is achieved by a chemical agent or light energy, the molecules may be cross-linked in the course of creating a mold or when peptide-containing solutions are applied to the body. Further, self-assembling peptide chains can be crosslinked to form a spider web-type pattern to reinforce the material in vivo. The crosslinks serve to reinforce the material providing increased rigidity and strength. For example, the self-assembling material can be applied to a wound, wherein the periphery of the material is functionalized with polymerizable groups. Upon crosslinking, the periphery of the material becomes more rigid, anchoring the material to the wound site, while the interior of material remains flexible to move as the body moves.

The half-life (e.g., the in vivo half-life) of the structures can also be modulated by incorporating protease or peptidase cleavage sites into the precursors that subsequently form a given structure. Proteases or peptidases that occur naturally in vivo or that are introduced (e.g., by a surgeon) can then promote degradation by cleaving their cognate substrates. The half-life can also be modulated by crosslinking (e.g., polymerization) of the material via functional groups within the material. These functional groups may be groups typically found in peptides or additional functional groups added to the peptides. Introducing crosslinks into the material typically increases the degradation time and can provide different cleavage sites/bonds within the material.

Either or both ends of a given peptide can be modified. For example, the carboxyl and/or amino groups of the carboxyl- and amino-terminal residues, respectively can be protected or not protected. The charge at a terminus can also be modified. For example, a group or radical such as an acyl group (RCO—, where R is an organic group (e.g., an acetyl group ($CH_3CO$—)) can be present at the N-terminus of a peptide to neutralize an "extra" positive charge that may otherwise be present (e.g., a charge not resulting from the side chain of the N-terminal amino acid). Similarly, a group such as an amine group (RNH—, where R is an organic group (e.g., an amino group —$NH_2$)) can be used to neutralize an "extra" negative charge that may otherwise be present at the C-terminus (e.g., a charge not resulting from the side chain of the C-terminal amino acid residue). Where an amine is used, the C-terminus bears an amide (—CONHR). The neutralization of charges on a terminus may facilitate self-assembly. One of ordinary skill in the art will be able to select other suitable groups.

Self-assembling peptides can be modified with additional domains that do not self-assemble. These additional domains can be derived from, for example, extracellular matrix components, cell adhesion molecules, cell surface receptors, growth factors, cytokines, chemokines, or combinations thereof. Examples of such modifications are disclosed in U.S. Patent Publication 2009/01624378 to Horii, et al. These embodiments can be used, for example, to promote differentiation of cells cultured in a nanofiber scaffold produced from the modified self-assembled peptides. Preferred self-assembling materials produce nanofiber scaffolds that can be used to maintain stem cells in an undifferentiated state for extended periods of time. Therefore, in preferred embodiments, the self-assembling peptides are not modified with amino acids derived from biologically active proteins.

Useful peptides can also be branched, in which case they will contain at least two amino acid polymers, each of which consists of at least three amino acid residues joined by peptide bonds. The two amino acid polymers may be linked by a bond other than a peptide bond.

Combinations of any of the modifications described here can be made. For example, self-assembling peptides that include a protease cleavage site and a cysteine residue and/or a cross-linking agent, kits and devices containing them, and methods of using them can be utilized.

The peptide structures formed from any self-assembling peptides made by any process can be characterized using various biophysical and optical techniques, such as circular dichroism (CD), dynamic light scattering, Fourier transform infrared (FTIR), atomic force (tension) microscopy (ATM), scanning electron microscopy (SEM), and transmission electron microscopy (TEM). For example, biophysical methods can be used to determine the degree of beta-sheet secondary structure in the peptide structure. Filament and pore size, fiber diameter, length, elasticity, and volume fraction can be determined using quantitative image analysis of scanning and/or transmission electron micrographs. The structures can also be examined using several standard mechanical testing techniques to measure the extent of swelling, the effect of pH and ion concentration on structure formation, the level of hydration under various conditions, the tensile strength, as well as the manner in which various characteristics change over the period of time required for the structures to form and degrade. These methods allow one of ordinary skill in the art to determine which of the various alternatives and peptides described herein are most suitable for use in the various methods, and allow optimization of the various processes.

Preferably, the self-assembling materials when they break down do not cause any secondary toxicity. Further, the break down product of the self-assembling materials would preferably be suitable for the growth and repair of the surrounding tissues.

Peptide-based structures can be formed of heterogeneous mixtures of peptides. In some embodiments, each of the types of peptides in the mixture is able to self-assemble alone. In other embodiments, one or more of each type of peptide would not, alone, self-assemble but the combination of heterogeneous peptides may self-assemble (i.e., peptides in the mixture are complementary and structurally compatible with each other). Thus, either a homogeneous mixture of self-complementary and self-compatible peptides of the same sequence or containing the same repeating subunit, or a heterogeneous mixture of different peptides which are complementary and structurally compatible to each other, can be used.

B. Non-Peptide Materials which Self-Assemble

1. Peptidomimetics and oligomers having backbones, which can Adopt Helical, Sheet, or Lattice Confirmations Another class of materials that can self-assemble are peptidomimetics. Peptidomimetics, as used herein, refers to molecules, which mimic peptide structure. Peptidomimetics have general features analogous to their parent structures, polypeptides, such as amphiphilicity. Examples of such peptidomimetic materials are described in Moore et al., *Chem. Rev.* 101(12), 3893-4012 (2001).

The peptidomimetic materials can be classified into four categories: α-peptides, β-peptides, γ-peptides, and δ-peptides. Copolymers of these peptides can also be used. Examples of α-peptide peptidomimetics include, but are not limited to, N,N'-linked oligoureas, oligopyrrolinones, oxazolidin-2-ones, azatides and azapeptides. Examples of β-peptides include, but are not limited to, β-peptide foldamers, β-aminoxy acids, sulfur-containing β-peptide analogues, and hydrazino peptides. Examples of γ-peptides include, but are not limited to, γ-peptide foldamers, oligoureas, oligocarbamates, and phosphodiesters. Examples of δ-peptides include, but are not limited to, alkene-based δ-amino acids and carbopeptoids, such as pyranose-based carbopeptoids and furanose-based carbopeptoids.

Another class of compounds that self-assemble includes oligomers having backbones, which can adopt helical or sheet conformations. Example of such compounds include, but are not limited to, compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination.

Examples of compounds containing backbones utilizing bipyridine segments include, but are not limited to, oligo (pyridine-pyrimidines), oligo(pyridine-pyrimidines) with hydrazal linkers, and pyridine-pyridazines.

Examples of compounds containing backbones utilizing solvophobic interactions include, but are not limited to, oligoguanidines, aedamers (structures which take advantage of the stacking properties of aromatic electron donor-acceptor interactions of covalently linked subunits) such as oligomers containing 1,4,5,8-naphthalene-tetracarboxylic diimide rings and 1,5-dialkoxynaphthalene rings, and cyclophanes such as substituted N-benzyl phenylpyridinium cyclophanes.

Examples of compounds containing backbones utilizing side chain interactions include, but are not limited to, oligothiophenes such as olihothiophenes with chiral p-phenyloxazoline side chains, and oligo(m-phenylene-ethynylene)s.

Examples of compound containing backbones utilizing hydrogen bonding interactions include, but are not limited to, aromatic amide backbones such as oligo(acylated 2,2'-bipyridine-3,3'-diamine)s and oligo(2,5-bis[2-aminophenyl] pyrazine)s, diaminopyridine backbones templated by cyanurate, and phenylene-pyridine-pyrimidine ethynylene backbones templated by isophthalic acid.

Examples of compounds containing backbones utilizing metal coordination include, but are not limited to, zinc bilinones, oligopyridines complexed with Co(II), Co(III), Cu(II), Ni(II), Pd(II), Cr(III), or Y(III), oligo(m-pheylene ethynylene)s containing metal-coordinating cyano groups, and hexapyrrins.

2. Nucleotidomimetics

Another class of molecules, which can self-assemble are nucleotidomimetics such as isomeric oligonucleotides, modified carbohydrates, nucleotides with modified nucleotide linkages, and nucleotides with alternative nucleobases.

Examples of isomeric nucleotides include, but are not limited to, iso-RNA and iso-DNA and α-DNA (change in the anomeric configuration from β to α), alt-DNA, and 1-DNA.

Examples of modified carbohydrates include, but are not limited to, backbones with C1'-bases connectivities such as tetrofuranosyl oligonucleotides, pentopyranosyl oligonucleotides, and hexopyranosyl oligonucleotides; backbones with C2'-base connectivities such as isonucleotides (repositioning of the base sugar connection from C1 to the C2 position), HNAs (insertion of an additional methylene group between the O4' and C1' position of a furanose), ANAs (incorporation of a C3'-(S)-hydroxyl group), MNAs (inversion of the C3'-OH configuration from (S) in ANAs to (R)), CNAs (replacement of the O of the hexose with a methylene group), CeNAs (introduction of a 5'-6' alkene within the analogous ring), as well as other ring systems, torsionally restricted oligonucleotides such as bicyclic oligonucleotides, LNAs (restriction of the pentofaranose backbone to the 3'-endo configuration), torsionally flexible oligonucleotides such as base sugar extensions (insertion of methylene and ethylene groups into both ?- and ?-deoxynucleotides) and acyclic backbones (glycerol derivatives incorporating phosphodiester linkages).

Examples of nucleotides with modified nucleotide linkages include, but are not limited to, PNAs (peptide nucleic acids), NDPs (nucleo-δ-peptides), fused sugar-base backbones, and cationic linkages.

Examples of alternative nucleobases include, but are not limited to, nucleotides with alternative aromatic nucleobases.

3. Other Materials

Other materials which can self-assemble include N-alkylacrylamide oligomers and di- and triblock co-polymers. N-alkylacrylamides can assume self-assembled into sheet-like structures (see Kendhale et al., *Chem. Comm.*,). Examples of block copolymers include copolypeptides, polypeptide-PEGS, PEO-polybutadienes, PEG-polysaccharides, etc.

Another class of materials which are known to self-assemble are dendrimers. "Dendrimers", as used herein, refers to branched polymers with successive shells of branch units surrounding central core. Dendrimers can self-assemble through a variety of different mechanisms, such as hydrogen bonding, ionic interactions, hydrophobic interactions, solvent interaction, side chain interactions, and the like. Non-limiting examples of self-assembling dendrimers are described in Zimmerman et al., *Science*, Vol. 271, No. 5252, 1095-1098 (1996); Zimmerman et al., *J. Am. Chem. Soc.*, 124(46), 13757-13769 (2002); and Frechet, *Proc. Nat. Acad. Sci.*, Vol. 99, No. 8, 4782-4787 (2002).

C. Preparation of Self-Assembling Peptides

The starting concentration of self-assembling peptide (SAP) effects the over all properties of the self-assembling peptide nanofiber scaffold (SAPNS) formed when the SAPs self-assemble. Depending on the formulation and desired properties of the macroscopic structure (e.g., the stiffness of the scaffold or the rate of its formation), the concentration of precursors (e.g., self-assembling peptides) can vary from approximately 0.01% w/v (0.1 mg/ml) to approximately 99.99% w/v (999.9 mg/ml), inclusive. For example, the concentration prior to scaffold formation can be between approximately 0.1% (1 mg/ml) and 10% (100 mg/ml), inclusive (e.g., about 0.1%-5%; 0.5%-5%; 1.0%; 1.5%; 2.0%; 2.5%; 3.0%; or 4.0% or more). In some embodiments, the concentration may be less than 0.1%. The precursors (e.g., self-assembling peptides) can be formulated as powders and administered in a powder form or resuspended. If dry, the peptides can then self-assemble following contact with bodily fluids (e.g., at a site of injury). In one embodiment, the concentration of the self-assembling peptides in any given formulation can vary and can be between approximately 0.1% (1 mg/ml) and 10% (100 mg/ml), inclusive. For example, the concentration of the self-assembling peptides (e.g., in a liquid formulation) can be approximately 0.1-3.0% (1-30 mg/ml) (e.g., 0.1-1.0%; 1.0-2.0%; 2.0-3.0% or 1.0-3.0%). The concentration of self-assembling peptides can be higher in stock solutions and in solid (e.g., powdered) formulations. In solid preparations, the concentration of self-assembling peptides can approach 100% (e.g., the concentration of self-assembling peptides can be 95, 96, 97, 98, 99% or more (e.g., 99.99%) of the composition). Whether in liquid or solid form, the peptides can be brought to the desired concentration prior to use by addition of a diluent (e.g., deionized water), powder, wetting agent, or a therapeutic, diagnostic or prophylactic agent.

Prior to self-assembly, the materials may be contained in (e.g., dissolved in) a solution that is substantially free of ions (e.g., monovalent ions) or that contains a sufficiently low concentration of ions to prevent significant self-assembly (e.g., a concentration of ions less than 10, 5, 1, or 0.1 mM). Self-assembly may be initiated or enhanced at any subsequent time by the addition of an ionic solute or diluent to a solution of the material or by a change in pH. For example, NaCl at a concentration of between approximately 5 mM and 5 M can induce the assembly of macroscopic structures within a short period of time (e.g., within a few minutes). Lower concentrations of NaCl may also induce assembly but at a slower rate. Alternatively, self-assembly may be initiated or enhanced by introducing the materials (whether dry, in a semi-solid gel, or dissolved in a liquid solution that is substantially free of ions) into a fluid (e.g., a physiological fluid such as blood or gastric juice) or an area (e.g., a body cavity such as the nose or mouth or a cavity exposed by a surgical procedure) comprising such ions. The gel does not have to be preformed prior to application to the desired site. Generally, self-assembly is expected to occur upon contacting the materials with such a solution in any manner.

A wide variety of ions, including anions and cations (whether divalent, monovalent, or trivalent), can be used. For example, one can promote a phase transition by exposure to monovalent cations such as $Li^+$, $Na^+$, $K^+$, and $Cs^+$. The concentration of such ions required to induce or enhance self-assembly is typically at least 5 mM (e.g., at least 10, 20, or 50 mM). Lower concentrations also facilitate assembly, although at a reduced rate. When desired, self-assembling materials can be delivered with a hydrophobic material (e.g., a pharmaceutically acceptable oil) in a concentration that permits self-assembly, but at a reduced rate. When self-assembling materials are mixed with a hydrophobic agent such as an oil or lipid the assembly of the material forms different structures. The structures will appear like ice on a layer of oil. In some cases when another material is added, the material will assemble into various other three dimensional structures that may be suitable for loading of a therapeutic agent. The hydrophilic part of the molecule will assemble in such a way as to minimize hydrophobic-hydrophilic interaction, thereby creating a barrier between the two environments. Several experiments have shown that the self-assembling materials will align on the surface of the oil like ice on water with the hydrophobic part of the molecule toward the surface and the hydrophilic portion of the molecule facing away from the oil, or will form toroidal like structures with the hydrophobic material contained inside. This type of behavior enables the encapsulation of therapeutics or other molecule of interested for delivery in the body.

Alternatively, some of the materials described herein do not require ions to self-assemble but may self assemble due to interactions with a solvent, hydrophobic interactions, side chain interactions, hydrogen bonding, and the like.

Depending on the formulation and desired properties of the macroscopic structure (e.g., the stiffness of the scaffold or the rate of its formation), the concentration of precursors (e.g., self-assembling materials) can vary from approximately 0.01% w/v (0.1 mg/ml) to approximately 99.99% w/v (999.9 mg/ml), inclusive. For example, the concentration prior to scaffold formation can be between approximately 0.1% (1 mg/ml) and 10% (100 mg/ml), inclusive (e.g., about 0.1%-5%; 0.5%-5%; 1.0%; 1.5%; 2.0%; 2.5%; 3.0%; or 4.0% or more). The precursors (e.g., self-assembling materials) can be formulated as powders and administered in a powder form or resuspended. If dry, the materials can then self-assemble following contact with bodily fluids (e.g., at a site of injury).

Peptide-based structures can be formed within regularly or irregularly-shaped molds, which may include a body cavity or a portion of the body (e.g., the lumen of a blood vessel) or which may be an inert material, including but not limited to, plastic or glass. The structures or scaffolds can be made to conform to a predetermined shape or to have a predetermined volume. To form a structure with a predetermined shape or volume (e.g., a desired geometry or dimension, including thin sheets or films), an aqueous peptide solution is placed in a pre-shaped casting mold, and the peptides are induced to self-assemble by the addition of a plurality of ions. Alternatively, the ions may be added to the peptide solution shortly before placing the solution into the mold, provided that care is taken to place the solution into the mold before substantial assembly occurs. Where the mold is a tissue (e.g., the lumen of a blood vessel or other compartment, whether in situ or not), the addition of an ionic solution may not be necessary. The resulting material characteristics, the time required for assembly, and the dimensions of the macroscopic structure that forms are governed by the concentration and amount of peptide solution that is applied, the concentration of ions used to induce assembly of the structure, and the dimensions of the casting apparatus. The scaffold can achieve a gel-like or substantially solid form at room temperature, and heat may be applied to facilitate the molding (e.g., one can heat a solution used in the molding process (e.g., a precursor-containing solution) to a temperature ranging up to about body temperature (approximately 37° C.)). Once the scaffold has reached the desired degree of firmness, it can be removed from the mold and used for a purpose described herein. The scaffold may be used to induce regeneration of tissues such as CNS (central nervous system), vessels, kidney, etc., The self-assembling material used for making scaffold for different tissues mimic the environment of the developing tissues and therefore can be different for each tissue.

In some embodiments, the self-assembling materials undergo a phase transition (e.g., a transition from a liquid state to a semi-solid, gel, etc.) when they come in contact with the body. In the case of skin, the compositions may be administered with an ionic solution or oil in order to self assemble, in the absence of moisture or oil on the skin. Self-assembly or phase transition is triggered by components found in a subject's body (e.g., ions) or by physiological pH and is assisted by physiological temperatures. Self-assembly or phase transition can begin when the compositions are exposed to or brought into contact with a subject's body and may be facilitated by the local application of heat to the area where the composition has been (or will be) deposited. The subject, for any indication described herein, can be a human. Based on studies to date, self-assembly occurs rapidly upon contact with internal bodily tissues without the application of additional heat. In one embodiment, the time required for effective assembly and/or phase transition can be 60 seconds or less following contact with a subject's internal tissues or to conditions similar to those found within the body (e.g., in 50, 40, 30, 20, or 10 seconds or less). In some circumstances, such as where the concentration of self-assembling agents in the composition is low or where the movement of the bodily substance is substantial, self-assembly or phase transition may take longer to achieve the desired effect, for example, up to a minute, 5 minutes, 10 minutes, 30 minutes, an hour, or longer. For example, a solution containing a self-assembling peptide applied to sites of blood vessel trans-section in the brain, liver, or muscle provides complete hemostasis within times as short as 10 seconds following application. Ion-containing solutions may be preferred when the compositions are used to protect a subject from contamination, as phase transitions do not occur, or do not readily occur, when non-ionic compositions contact intact skin.

The compositions can form structures that are substantially rigid (e.g., solid or nearly solid) or that assume a definite shape and volume (e.g., structures that conform to the shape and volume of the location to which a liquid composition was administered, whether in vivo or ex vivo). The solidified material may be somewhat deformable or compressible after assembly or phase transition, but will not substantially flow from one area to another, as compositions at a different point along the liquid to solid continuum may do, which may be due, at least in part, to their ability to undergo phase transitions. As a result, the compositions can be used to prevent the movement of a bodily substance in a subject in need thereof. Self-assembly can be achieved in vivo or ex vivo by exposure to conditions within a certain range of physiological values (e.g., conditions appropriate for cell or tissue culture) or non-physiological conditions. "Non-physiological conditions" refers to conditions within the body or at a particular site that deviate from normal physiological conditions at that site. Such conditions may result from trauma, surgery, injury, infection, or a disease, disorder, or condition. For example, a puncture wound in the stomach generally results in a decrease in the pH as stomach acid flows into the wound site. The materials described herein should self assemble under such conditions. While liquid formulations are readily dispensed, the compositions administered may also be in a gel form that may become stiffer upon contact with the subject's body.

Regardless of the precise nature of the self-assembling agents, upon exposure to conditions such as those described herein, the agents can form membranous two- or three-dimensional structures including a stable macroscopic porous matrix having ordered or unordered interwoven nanofibers (e.g., fibers approximately 10-20 nm in diameter, with a pore size of about 50-100 nm or larger in a linear dimension). Three-dimensional macroscopic matrices can have dimensions large enough to be visible under low magnification (e.g., about 10-fold or less), and the membranous structures can be visible to the naked eye, even if transparent. Although three-dimensional, the structures can be exceedingly thin, including a limited number of layers of molecules (e.g., 2, 3, or more layers of molecules). Typically, each dimension of a given structure will be at least 10 µm in size (e.g., two dimensions of at least 100-1000 µm in size (e.g., 1-10 mm, 10-100 mm, or more)). The relevant dimensions may be expressed as length, width, depth, breadth, height, radius, diameter, or circumference in the case of structures that have a substantially regular shape (e.g., where the structure is a sphere, cylinder, cube, or the like) or an approximation of any of the foregoing where the structures do not have a regular shape.

The self-assembling peptides can form a hydrated material when contacted with water under conditions such as those described herein (e.g., in the presence of a sufficient concentration (e.g., physiological concentrations) of ions (e.g., monovalent cations)). The materials may have a high water content (e.g., approximately 95% or more (e.g., approximately 97%, 98%, 99% or more)), and the compositions can be hydrated but not substantially self-assembled. A given value may be "approximate" in recognition of the fact that measurements can vary depending, for example, on the circumstances under which they are made and the skill of the person taking the measurement. Generally, a first value is approximately equal to a second when the first falls within 10% of the second (whether greater than or less than) unless it is otherwise clear from the context that a value is not approximate or where, for example, such value would exceed 100% of a possible value.

The properties and mechanical strength of the structures or scaffolds can be controlled as required through manipulation of the components therein. For example, the stiffness of an assembled gel can be increased by increasing the concentration of self-assembling agents (e.g., peptides) therein. Alternatively, it may be desirable for different parts of the material to have different mechanical properties. For example, it may be advantageous to decrease the stability of all or part of the material by manipulating the amino acid sequence. This may be desirable when the materials are used to fill a void, such that the edges of the material self-assemble to attach to the tissue site while the rest of the material flows out into the void.

The compositions can be formulated as concentrated stocks or in dry form, and these can be diluted or dissolved to form compositions (e.g., biocompatible compositions), which are substantially non-toxic to biological cells in vitro or in vivo. For example, the compositions can contain materials in quantities that do not elicit a significant deleterious effect on the recipient's body (e.g., a prohibitively severe immunological or inflammatory reaction, or unacceptable scar tissue formation).

When a solution containing non-assembled peptides is laid down on a biological tissue, the peptides having sufficient proximity to the tissue assemble, causing the solution to self-assemble. Any solution that remains distant from the tissue remains liquid, as the self-assembling peptides have not yet been exposed to conditions that promote their assembly. As the material is disturbed (e.g., by performing a surgical procedure), liquid material appears to gel as it comes into sufficient contact with the body. At times, the compositions can take on characteristics ranging from a liquid to those of a solid, appearing gel- or salve-like or as a slurry).

D. Cells

Self-assembling materials (e.g., SAPs) can be combined, prior to, during, or after self-assembly, with cells to further enhance the repair or replacement of diseased or damaged tissues. The cell may be stem cells, progenitor cells, or partially or completely differentiated cells. The cells are preferably human to reduce the risk of an immune response. Stem cells include embryonic and adult stem cells including umbilical chord stem cells, peripheral blood stem cells, bone marrow stem cells, stromal cells, parenchymal cells, mesenchymal stem cells, liver reserve cells, neural stem cells, and pancreatic stem cells. Stem cells are also differentiated cells that are reprogrammed to an embryonic-like state by transfer of nuclear contents into oocytes or by fusion with embryonic stem (ES) cells. For example, the induction of pluripotent stem cells from mouse embryonic or adult fibroblasts is accomplished by introducing one or more of the following factors, Oct3/4, Sox2, c-Myc, Klf4, and Nanog. Following contact with such factors, differentiated cells are reprogrammed and exhibit the morphology and growth properties of stem cells, e.g., ES cells, and express stem cell marker genes.

Examples of progenitor cells include those that give rise to blood cells, neural progenitor cells, fibroblasts, endothelial cells, epithelial cells, smooth muscle cells, skeletal muscle cells, cardiac muscle cells, multi-potential progenitor cells, pericytes, endothelial cells, chondrocytes, and osteogenic cells. Therefore, in some embodiments, the stem cells can differentiate into neurocytes, cardiocytes, myocytes, chondrocytes, endothelial cells, osteocytes, or a combination thereof. In a preferred embodiment, the stem cells can differentiate into at least neurocytes such as neurons, glia, astrocytes. The population of progenitor cells can be selected based on the cell type of the intended tissue to be repaired. For example, if skin is to be repaired, the population of progenitor cells will give rise to non-keratinized epithelial cells or if cardiac tissue is to be repaired, the progenitor cells can produce cardiac muscle cells. The matrix composition can also be seeded with autogenous cells isolated from the patient to be treated. In an alternative embodiment the cells may be xenogeneic or allogeneic in nature.

The cells may be genetically modified or engineered. The cells may be engineered to express a target gene product which is biologically active which provides a chosen biological function, which acts as a reporter of a chosen physiological condition, which augments deficient or defective expression of a gene product, or which provides an anti-viral, anti-bacterial, anti-microbial, or anti-cancer activity. The target gene product may be a peptide or protein, such as an enzyme, hormone, cytokine, antigen, or antibody, a regulatory protein, such as a transcription factor or DNA binding protein, a structural protein, such as a cell surface protein, or the target gene product may be a nucleic acid such as a ribosome or antisense molecule. The target gene products include, but are not limited to, gene products which enhance cell growth. For example, the genetic modification may upregulate an endogenous protein, introduce a new protein or regulate ion concentration by expressing a heterologous ion channel or altering endogenous ion channel function. Examples include, but are not limited to, engineered tissues that express gene products which are delivered systemically (e.g., secreted gene products such as proteins including growth factors, hormones, Factor VIII, Factor IX, neurotransmitters, and enkaphalins).

For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS).

Optionally, the self-assembling material or SAPNS is seeded with two or more substantially pure populations of cells. The populations can be spatially or physically separated, or the populations can be mixed or otherwise allowed to come into contact with one another. The SAPNS not only provides a surface upon which or within cells are seeded/attached but indirectly affects production/education of cell populations by housing a second (third, or several) cell population(s) with which a first population of cells associates (cell-cell adhesion). Such "accessory" cell populations secrete desirable cytokines, growth factors or other signaling molecules, and/or deposit appropriate extracellular matrix proteins. The population or populations of accessory cells can be selected based on the cell type of the intended tissue to be repaired. For example, if neuronal tissue is to be repaired, accessory cell populations may consist of Schwann cells or astrocytes.

E. Therapeutic, Diagnostic and Prophylactic Agents

The self-assembling material or SAPNS formulations may contain one or more therapeutic, prophylactic or diagnostic agents. The agents can be peptides or proteins, polysaccharides or saccharides, nucleic acids or nucleotides, proteoglycans, lipids, carbohydrates, or small molecules, typically organic compounds having multiple carbon-carbon bonds. Small molecules have relatively low molecular weights (e.g., less than about 1500 g/mol) and are not peptides or nucleic acids. The agent(s) may be naturally occurring or prepared via chemical synthesis. For example, a protein having a sequence that has not been found in nature (e.g., one that does not occur in a publicly available database of sequences) or that has a known sequence modified in an unnatural way by a human hand (e.g., a sequence modified by altering a post-translational process such as glycosylation) is a synthetic molecule. Nucleic acid molecules encoding such proteins (e.g., an oligonucleotide, optionally contained within an expression vector) can be incorporated into the compositions described herein. For example, a composition can include a plurality of self-assembling peptides and cells that express, or that are engineered to express, a protein (by virtue of containing a nucleic acid sequence that encodes the protein).

The one or more therapeutic, prophylactic or diagnostic agents can be added in combination or alternation with the self-assembling peptides. In certain embodiments, the one or more therapeutic, prophylactic or diagnostic agents can be covalently linked to the self-assembling peptides, for example, via a thio-linkage or other suitable linkages.

In one embodiment, these agents may be anti-inflammatories, vasoactive agents, coloring agents, anti-infectives, anesthetics, growth factors, and/or cells, as discussed above.

Representative vasoconstrictors, any of which can be formulated with one or more self-assembling peptides (e.g., in a biocompatible composition in liquid, powder or gel form) include, but are not limited to, epinephrine and phenylephrine.

Representative anesthetic agents include, but are not limited to, benzocaine, bupivacaine, butamben picrate, chloroprocaine, cocaine, curare, dibucaine, dyclonine, etidocaine, lidocaine, mepivacaine, pramoxine, prilocaine, procaine, propoxycaine, ropivacaine, tetracaine, or combinations thereof. Local application of the anesthetic agent may be all that is required in some situations, for example, for a burn or other wound to the skin, including decubitus ulcers, or for minimally invasive surgeries. Combining local anesthetics with the self-assembling peptides, whether combined by virtue of being present in the same formulation or by virtue of co-administration, can help contain the anesthetic within the body and reduce the amount entering the circulation. Vasoconstrictors such as phenylephrine can be included to prolong the effect of local anesthesia (e.g., 0.1-0.5% phenylephrine). Analgesic agents other than a local anesthetic agent, such as steroids, non-steroidal anti-inflammatory agents like indomethacin, platelet activating factor (PAF) inhibitors such as lexipafant, CV 3988, and/or PAF receptor inhibitors such as SRI63-441.

An anti-infective or antimicrobial agent (e.g., an antibiotic, antibacterial, antiviral, and/or antifungal agent) can be included for either systemic or local administration. Examples include β-lactam antibiotics such as penicillins and cephalosporins and other inhibitors of cell wall synthesis such as vancomycin, chloramphenicol, tetracyclines, macrolides, clindamyin, streptogramins, aminoglycosides, spectinomycin, sulfonamides, trimethoprim, quinolones, amphotericin B, flucytosine, azoles such as ketoconazole, itraconazole, fluconazole, clotrimazole, and miconazole, griseofulvin, terbinafine, and nystatin. The antimicrobial can be topically administered, e.g., to treat skin infections or burns, or to help prevent infection at a site of catheter insertion (e.g., an intravenous catheter). Examples of topical antibiotics include kanamycin, neomycin, bacitracin, polymixin, topical sulfonamides such as mafenide acetate or silver sulfadiazine, or gentamicin sulfate. The antimicrobial can be a broad spectrum agent such as a second, third, or fourth generation cephalosporin can be used. The antibiotics may be active against a wide range of bacteria including both gram positive and gram negative species. Such antibacterial agents may be particularly appropriate where scaffolds are used to inhibit movement of intestinal contents such as during intestinal resection or other surgery that purposefully or accidentally disturbs the integrity of the intestinal wall. One of ordinary skill in the art will be able to select appropriate antimicrobial agents by considering factors such as the patient's history (e.g., any history of an allergic reaction to such agents), the location to which the peptides are to be applied, the type of infectious agent likely to be present, and so forth.

Suitable coloring agents to show uniformity and extent of application of the self-assembling peptides include commercially available food colorings, natural and synthetic dyes, and fluorescent molecules. Preferably, the coloring agent is nontoxic or is included at such low concentrations as to minimize any undesirable effect (e.g., a toxic effect). The use of a coloring agent allows for improved visualization of an area that is covered by a structure or scaffold and can facilitate removal, if such removal is desired. The coloring agent can be one that changes color when it comes into contact with a contaminated area (e.g., a color change may be triggered by the contamination itself (e.g., by the blood or bacteria present at a wound site)). For example, a metabolic product of a bacterium may trigger a color change. Conditions such as pH or redox state induced by contaminants may also be detected. Exemplary coloring agents include, but are not limited to, azo red, azo yellow, arsenazo III, chlorophosphonazo III, antipyrylazo III, murexide, Eriochrome Black T and Eriochrome Blue SE for $Mg^{2+}$, oxyacetazo I, carboxyazo III, tropolone, methylthymol blue, and Mordant Black 32. AlamarBlue, a redox indicator, and phenol red can also be used in the compositions and methods described herein.

Bioactive therapeutic substances include, but are not limited to, growth factors, hormones, neurotransmitters, neurotransmitter or growth factor receptors, interferons, interleukins, chemokines, cytokines, colony stimulating factors, chemotactic factors, MMP-sensitive substrate, fibrin, extracellular matrix components such as collagen, fibronectin, vitronectin, hyaluronic acid, adhesion peptides such as RGD-containing peptides or polypeptides, and angiogenic factors such as angiopoietin. Splice variants of any of the above mentioned proteins, and small molecule agonists or antagonists thereof that may be used advantageously to alter the local balance of pro and anti-migration and differentiation signals may also be used. One or more growth factors can be included to accelerate one or more aspects of healing (e.g., angiogenesis, cell migration, process extension, and cell proliferation).

The one or more growth factors can be incorporated into the self-assembling material or may be co-administered with the self-assembling composition. Examples of growth factors include, but are not limited to, vascular endothelial growth factor (VEGF), bone morphogenetic protein (BMP), a transforming growth factor (TGF) such as transforming growth factor β, a platelet derived growth factor (PDGF), an epidermal growth factor (EGF), a nerve growth factor (NGF), an insulin-like growth factor (e.g., insulin-like growth factor I), scatter factor/hepatocyte growth factor (HGF), granulocyte/macrophage colony stimulating factor (GMCSF), a glial growth factor (GGF), a fibroblast growth factor (FGF), etc. It will be appreciated that in many cases these terms refer to a variety of different molecular species. For example, several transforming growth factor β species are known in the art. One of ordinary skill in the art will be guided in the selection of an appropriate growth factor by considering, for example, the cell type(s) contained within the scaffold, or alternatively, the site at which the composition is to be administered. For example, an EGF can be included in compositions applied to the skin; an NGF and/or GGF can be included in compositions applied to nerves or the nervous system; and so forth.

Examples of cytokines include, but are not limited to, IL-1, IL-2, IL-4, IL-5, IL-6, IL-7, IL-10, IL-12, IL-15, IL-18, granulocyte-macrophage colony stimulating factor (GM-CSF), granulocyte colony stimulating factor (G-CSF), interferon-gamma, IFN-alpha, tumor necrosis factor (TNF), TGF-beta, FLT-3 ligand, and CD40 ligand.

The growth factor, cytokine or other agent can be a chemotactic substance, which has the ability, in vivo or in cell culture, to recruit cells to a site at which the substance is present. The cells recruited may have the potential to contribute to the formation of new tissue or to repair existing, damaged tissue (e.g., by contributing structurally and/or functionally to the tissue (e.g., by providing growth factors or contributing to a desirable immune response)). Certain chemotactic substances can also function as proliferation agents (e.g., neurotropic factors such as NGF or BDNF).

For some embodiments, the compositions include at least one cell growth factor that prevents premature terminal differentiation of the transplanted cells. The choice of growth factor will depend upon the type of cells and the influence of a particular growth factor on those cells such that the cells are directed to bypass their normal tendency to differentiate, and remain in a proliferative phase until a sufficient number of cells is attained to regenerate the targeted tissue and for the cells to have also migrated from the scaffold. Splice variants of any of the above mentioned proteins, and small molecule agonists or antagonists thereof that may be used advantageously to alter the local balance of pro and anti-migration and differentiation signals are also contemplated herein.

Other agents include cyanoacrylates, oxidized cellulose, fibrin sealants, collagen gel, thrombin powder, microporous polysaccharide powders, clotting factors (e.g., Factor V, Factor VIII, fibrinogen, or prothrombin) and zeolite powders which facilitate formation or physical properties of the self-assembling peptides.

It will be understood that therapeutic, prophylactic or diagnostic molecules are generally administered in an effective amount in order to achieve a clinically significant result, and effective dosages and concentrations are known in the art. These dosages and concentrations can guide the selection of dosages and concentrations in the present context. Bioactive molecules can be provided at a variety of suitable concentrations and in suitable amounts (e.g., in the microgram or milligram range, or greater). For guidance, one can consult texts such as Goodman and Gilman's *The Pharmacological Basis of Therapeutics,* 10th Ed., and Katzung, *Basic and Clinical Pharmacology.*

F. Media

Cell culture media formulations for culturing cells on SAPNS are well known in the literature and many are commercially available. Preconditioned media ingredients include, but are not limited to, those described below. Additionally, the concentration of the ingredients are well known to one of ordinary skill in the art. See, for example, Methods For Preparation Of Media, Supplements and Substrate for Serum-free Animal Cell Cultures. The ingredients include amino-acids (both D and/or L-amino acids) such as glutamine, alanine, arginine, asparagine, cystine, glutamic acid, glycine, histidine, isoleucine, leucine, lysine, methionine, phenylalanine, proline, serine, threonine, tryptophan, tyrosine, and valine and their derivatives; acid soluble subgroups such as thiamine, ascorbic acid, ferric compounds, ferrous compounds, purines, glutathione and monobasic sodium phosphates. Additional ingredients include sugars, deoxyribose, ribose, nucleosides, water soluble vitamins, riboflavin, salts, trace metals, lipids, acetate salts, phosphate salts, HEPES, phenol red, pyruvate salts and buffers. Other ingredients often used in media formulations include fat soluble vitamins (including A, D, E and K) steroids and their derivatives, cholesterol, fatty acids and lipids Tween® 80, 2-mercaptoethanol pyramidines as well as a variety of supplements including serum (fetal, horse, calf, etc.), proteins (insulin, transferrin, growth factors, hormones, etc.) antibiotics (gentamicin, penicillin, streptomycin, amphotericin B, etc.) whole egg ultra filtrate, and attachment factors (fibronectins, vitronectins, collagens, laminins, tenascins, etc.).

G. Excipients, Carriers, and Devices

The compositions can include a pharmaceutically acceptable carrier. In one embodiment, the self-assembling peptide is provided as a dry or lyophilized powder which can be administered directly as a powder which hydrates at the site of application. Alternatively, the formulation is suspended or dissolved in a solvent, most preferably aqueous, most preferably a pharmaceutically acceptable aqueous buffer or sterile saline and applied as a spray, paint, or injection. The formulation can also by administered in a hydrogel such as chitin, collagen, alginate, or a synthetic polymer. Any formulation suitable for application to the skin (e.g., a liquid, which can be applied as a spray or a powder) can be used. Compositions that include cells should be compatible with cell viability.

III. Methods of Use

A. Inhibition of Proliferation

The formulations can be used to inhibit proliferation, taking into account that different cell types proliferate at different rates.

1. Self-Assembling Peptide Nanofiber Scaffolds

SAPNS reduce or inhibit proliferation of cells relative to proliferation in the absence of SAPNS. The concentration of SAPNS can be adjusted to control the rate of proliferation. This is because control of cell proliferation is cell-cell contact, and SAPNS can be used to mimic cell-cell contact with cells. As the concentration of SAPNS increases, proliferation is inhibited for longer periods of time. In one embodiment, SAPNS are used to induce senescence or quiescence in cells. Senescence and quiescence, in this sense, are both characterized by a lack of proliferation. The concentration of SAPNS is also used to delay the on-set of proliferation of cells. In some embodiments, the self-assembling peptides are present from 0.01 to 5% wt/vol. In a preferred embodiment the self-assembling polypeptide is RADA16-I. In some embodiments, proliferation is delayed between 1 and 30 days. Preferably, proliferation is delayed between 1 and 15 days.

In one embodiment 0.5% SAPNS can be used to delay proliferation between about 1 and 3 days. Alternatively, 1.0% SAPNS is used to delay proliferation between about 3 and 5 days. 2% SAPNS can be used to delay proliferation between 5 and 7 days. In a preferred embodiment, the concentration of SAPNS is between 0.5% and 2%, cells are neural cells, morphology is changed and proliferation is delayed between 1 and 7 days.

2. Serum

As illustrated in Example 1 below, the presence or absence of serum is used to further fine-tune the rate of proliferation of cells in SAPNS. The presence of serum decreases the inhibition or delay in proliferation induced by SAPNS. Suitable serums are known to one skilled in the art and include, but are not limited to, Fetal Bovine Serum; Fetal Bovine Serum, Qualified for Human Embryonic Stem Cells; Fetal Bovine Serum, Tet System Approved Fetal Bovine Serum, Heat Inactivated; Fetal Bovine Serum, Dialyzed Fetal Bovine Serum; Newborn Calf Serum; Charcoal Stripped Special Newborn Calf Serum (Less than 10 days); Heat Inactivated Adult Bovine Serum Donor Horse Serum; Heat Inactivated Porcine Serum; and Rabbit Serum. Preferably the serum is Fetal Bovine Serum. The concentration of serum in a suitable, tissue compatible solution or media is between 0.1-25%, preferably between 1% and 12%, most preferably 10%. In a preferred embodiment, the serum is 10% Fetal Bovine Serum.

In some embodiments, the self-assembling peptides are present from 0.01 to 5% wt/vol. In a preferred embodiment the self-assembling polypeptide is RADA16-I. In some embodiments, proliferation is delayed between 1 and 30 days. In one embodiment 0.5% SAPNS in the absence of serum delays proliferation of neural cells about 3 days. In another embodiment, 0.5% SAPNS in the presence of serum delays proliferation of neural cells by about 1 days. In still another embodiment 1% SAPNS in the absence of serum delays proliferation of neural cells about 5 days. 1% SAPNS in the presence of serum delays proliferation of neural cells about 3 days. 2% SAPNS in the absence of serum delays proliferation of neural cells about 7 days. In another embodiment, 2% SAPNS in the presence of serum changes morphology, and delays proliferation of neural cells about 5 days.

B. Delayed Differentiation

SAPNS also affect the rate of cellular differentiation relative to cells in the absence of SAPNS. SAPNS can inhibit or reduce the rate of differentiation. The rate of differentiation can include the extent of differentiation, and length of time it takes to reach terminal differentiation. This may be important for storage of stem cells, or allowing transplanted stem cells to acclimate to their environment prior to differentiation.

1. Self-Assembling Peptide Nanofiber Scaffolds

Figure 2:
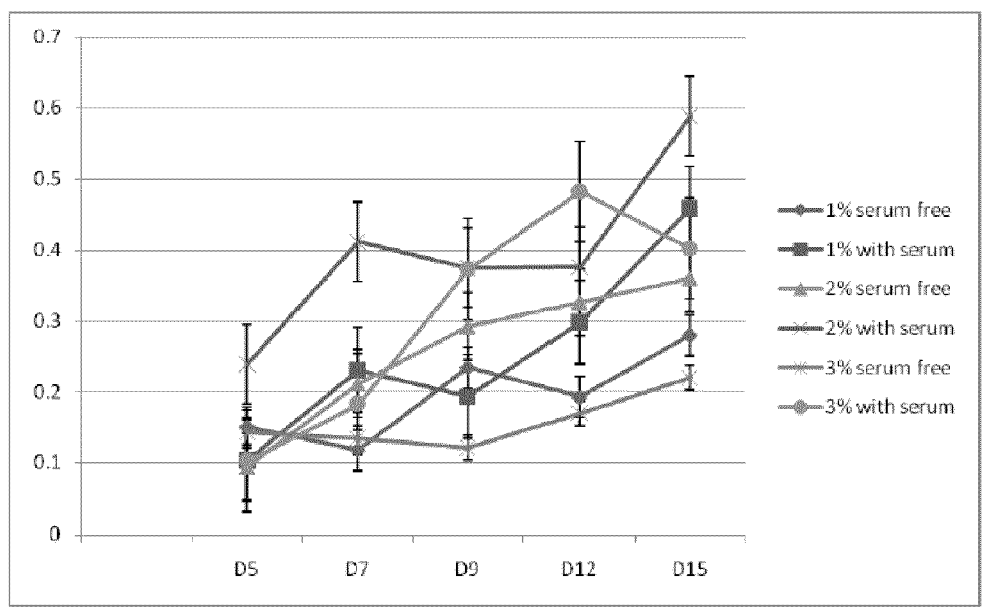
FIG. 2 is a line graph illustrating the percentage of processes in neural precursor cells that have branches verses time (days). The percentage of branches is represented by units, for example 0.7 units is equal to 70%. Closed diamonds represent 1% SAPNS in serum free media. Closed squares represent 1% SAPNS in media with serum. Closed triangles represent 2% SAPNS in serum free media. "X"s represent 1% SAPNS in media with serum. "Asterisks/stars" represent 3% SAPNS in serum free media. Closed circles represent 3% SAPNS in media with serum.
Figure 3:
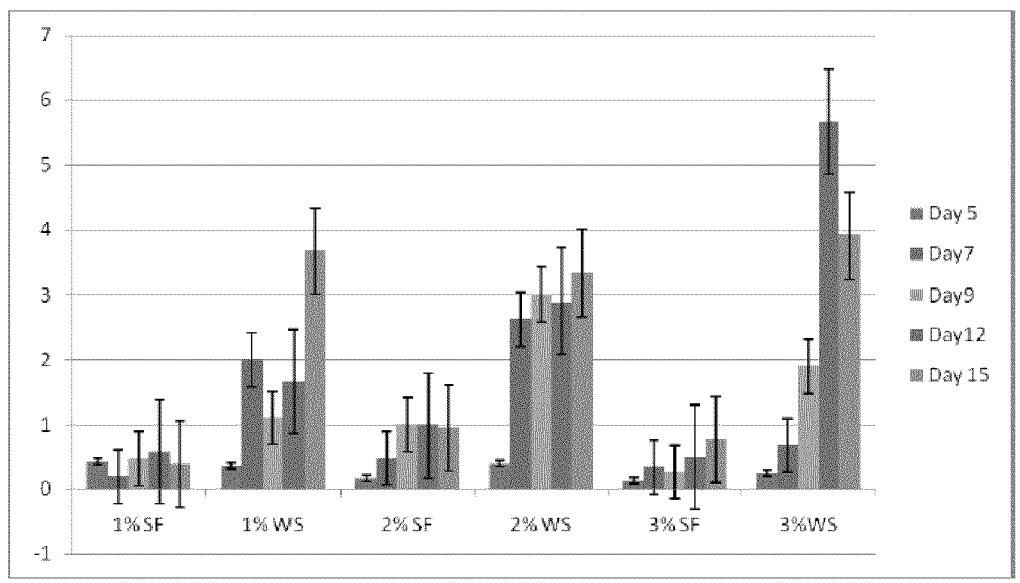
FIG. 3 is a bar graph illustrating the number of branched processes per neural precursor cell verses time (days). Six culture conditions occupy the x-axis. Moving left to right the six culture conditions are 1% SAPNS in serum free media, 1% SAPNS in media with serum, 2% SAPNS in serum free media, 2% SAPNS in media with serum, 3% SAPNS in serum free media, 3% SAPNS in media with serum. Each culture condition is populated with five bars, representing five time points. Moving left to right within each culture condition, the bars represent day 5, day 7, day 9, day 12, and day 15. Error bars=standard error.

The concentration of SAPNS can be adjusted to control the rate of differentiation. In the absence of serum, cellular differentiation is reduced compared to cells grown in the presence of serum at the same concentration of SAPNS (FIGS. 1-3). SAPNS can be used to maintain the totipotent potential of cells. SAPNS can be used to maintain the pluripotent potential of cells. SAPNS can be used to maintain the multipotent potential of cells. SAPNS can be used to maintain the progenitor potential of cells. This affect is illustrated in Examples 1 and 3 below. In some embodiments, the self-assembling peptides are present from 0.01 to 5% wt/vol. In a preferred embodiment the self-assembling polypeptide is RADA16-I. In some embodiments, differentiation is delayed between 1 and 30 days. In another embodiment differentiation is reduced for between 1 and 15 days. In another embodiment, between about 0.5% and 3% SAPNS is used to reduce differentiation for at least 15 days. In another embodiment, between about 0.5% and 3% SAPNS in the absence of serum is used to inhibit, delay, or reduce process extension in neural cells for about between 1 and 30 days.

2. Serum

The presence or absence of serum can be used to further fine-tune the rate of differentiation of cells in SAPNS. This affect is illustrated in Examples 1 and 3 below. The addition of serum increases the rate of differentiation relative to its absence. Preferred serums and serum concentrations are described above. In one embodiment, the addition of serum increases the frequency of process extension in neural cells. In the absence of serum, higher concentrations of SAPNS are more effective at inhibiting or reducing differentiation than lower concentrations of SAPNS. For example, at higher concentrations of SAPNS, process growth is reduced, and the number of process extensions and percentage of processes with branches are decreased relative to serum conditions. This affect is illustrated in Examples 1 and 3 below.

3. pH

The pH of the materials is preferably buffered. pH contributes to the delay of cell growth and differentiation. This is exemplified in Examples 4 and 5 below. Untreated SAPNS has a low pH of approximately 3-4. If the material is not properly buffered, then there will be an acid shock; the cells that are in the implant of SAPNS will slowly disappear. Blood and bodily fluids, such as cerebral spinal fluid, can contribute to the buffering of implants in vivo. Alternatively, buffered solution can be applied to SAPNS and/or cells prior to growth in vitro, or placement in vivo.

Suitable buffering agents, including aqueous buffering solutions, can bring the SAPNS to a pH between 5-9, preferably between 6-8, most preferably between 7-8. The buffer solution may contain other ingredients such as saccharides, polymeric substances, chemical substances, and biological substances in addition to the buffer agent. The pH of the buffer solution can be adjusted with an acid (e.g., HCl) or an alkali (e.g., NaOH or KOH), or by mixing at an appropriate ratio compounds that show different pH values, e.g., monosodium salt and disodium salt of a polybasic acid. In one embodiment the buffering solution is a phosphate buffer. In a preferred embodiment the buffering solution is tissue culture media, and the pH is buffered to a physiological pH between 7.2 and 7.6.

4. Number of Cells

The number of cells present in SAPNS also affects the rate of differentiation. There appears to be a similar reaction to the concentration of the material and the cell density that decreases proliferation and differentiation. By manipulating the concentration of cells, the environment of early development can be mimicked, and they will remain in stasis for an extended period of time until induced to differentiate. In some embodiments, the self-assembling peptides are present from 0.01 to 5% wt/vol. In a preferred embodiment the self-assembling polypeptide is RADA16-I. In one embodiment, the concentration of cells is used to inhibit or delay differentiation. In some embodiments, differentiation is delayed between 1 and 30 days. In another embodiment differentiation is reduced for between 1 and 15 days. In a preferred embodiment, the concentration of cells can be 1,000 cells/µl to 100,000 cells/µl, including about 1,000 to 30,000 cells/µl, 1,000 to 20,000 cells/µl, 1,000 to 10,000 cells/µl, and 5,000 to 20,000 cells/µl. Therefore, the concentration of cells can be about 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000 cells/µl.

C. Migration

SAPNS do not covalently bond but are held together by weak ionic and van der Waal's interactions. These interactions allow the material to self-assemble along the hydrophobic backbone, and hydrophilic fingers which stick out perpendicular to the direction of the fiber. The edges of the fiber are exposed and when a cell interacts with the fiber, it causes a destabilization of the extracellular nanoenvironment at the contact point with the fiber. The fiber disassembles to allow the cell to migrate into it, and then reassembles on the other side of the cell.

In one embodiment the concentration of the SAPNS is adjusted to modulate migration of host cells into the treated area.

D. Maintenance and Storage of Cells in Culture

The compositions can be used to culture cells, such as stem cells, in vitro. Self-assembling peptides can be used to form two or three dimensional scaffolds (SAPNS) that support cellular viability and growth, but delay differentiation. Using the tunable parameters described above, cells can be maintained in vitro indefinitely. Self-assembling peptides can be induced to form scaffolds on sterile glass or plastic dishes, or other surfaces or containers suitable for tissue or cell culture. Cells are seeded onto or encapsulated in SAPNS and cultured according to standard protocols such as those described in the examples below or *Current Protocols in Cell Biology*, published by Wiley Interscience. In some embodiments the cells are explanted tissues or organs. Importantly, unlike traditional stem cell culture, cells of the present compositions can be maintained or stored in the absence of serum or feeder-layers. In one embodiment, cells cultured on or encapsulated in SAPNS can be maintained as undifferentiated cells in a quiescent or senescent state by excluding serum from the media. In another embodiment, serum can be introduced to induce proliferation or differentiation of cultured cells. In another embodiment, a concentration of SAPNS is selected to control the rate of differentiation of cells.

E. Tissue Engineering/Organ Culture

The compositions can be used to generate or prepare tissue or organs for transplantation in vivo. Cells can be stems cells, progenitor cells, or differentiated cells. The type of cell or cells selected will be known to one of skill in the art based on the desired tissue or organ, (e.g. if cardiac tissue is desired, cardiomyocytes may be selected). Cells are also selected to be permissive to implantation in the recipient (e.g. to prevent graft rejection or graft-verse-host disease). In one embodiment the cells are donor tissue or organ explants. In one embodiment the concentration of SAPNS is manipulated to control proliferation or differentiation. In another embodiment stem cells or progenitor cells can be induced to differentiate in culture according to the methods described above. The compositions can be cultured in a regular or irregular-shaped mold to create tissue that is in the shape of mold. Selection of a mold will be known to one of skill in the art based on the desired implant (e.g., the lumen of a blood vessel).

After creating the implant in vitro, the resulting cells, tissue, or organ implants are grafted into or onto a recipient. Methods for performing surgical transplants will be known to one of skill in the art, and may include both invasive (e.g. "open" surgery), and minimally or non-invasive methods. Minimally invasive surgical techniques include, but are not limited to, hypodermic injection, air-pressure injection, subdermal implants, percutaneous surgery, laparoscopic surgery, arthroscopic surgery, microsurgery, keyhole surgery, endoscopy, and endovascular surgery. In some embodiments cells are maintained as stem cells or progenitor cells prior to and during implantation, using the methods described above. This may be desirable because maintaining cells of the implant in an undifferentiated, quiescent state provides an opportunity for reprogramming, delay of growth program, or protection of the implanted cells. In one embodiment, the composition is designed to allow for infiltration of host cells into the implant to facilitate reprogramming of the implanted cells. SAPNS are recognized by the body as "self," and are tolerated when grafted into the body.

F. Repair of Injured, Diseased, or Defective Tissue

An effective amount of the compositions can be used in the treatment of injured, diseased, or defective tissue. In one embodiment, tissue is surgically repaired or replaced using tissue implants as described above. In another embodiment, the compositions are administered by injection. Examples of injured, diseased, or defective tissue and organs that can be treated include, but are not limited to, brain, spinal chord, muscle, heart, lung, kidney, liver, pancreas, skin, cornea, hematopoietic stem cells, bone, cartilage, uterus, bowel, islets of langerhans, ovary, fascia, pericardium, sclera, and vascular tissue, whole or in part (e.g. individual cell types associated with each organ).

G. Wound Repair

The compositions are used to facilitate wound repair. Studies indicate that self-assembling peptides have the ability to enhance healing, particularly of an epithelial layer or muscle, and can therefore be administered to treat a site of tissue damage (see U.S. Published Application No. 2008/0174979). For example, one can apply a composition including self-assembling peptides and cells to the site of tissue damage. The compositions can be used for either acute or chronic wound care. For example, they can be applied to skin wounded in any manner (e.g., lacerated or burned) and to lesions such as diabetic ulcers and pressure sores.

In another embodiment, the compositions are used in neuronal repair and regeneration. Methods for repairing brain and spinal chord lesions are described in Examples 4 and 5 below and in U.S. Patent Publication No. 2005/0287186 and Guo, et al., *Neurology Nanomedicine*, 3:311-321, (2007). Compositions including self-assembling peptides and cells can be implanted at the site of injury to facilitate gap closure and neuronal repair or regeneration. The compositions help to program, or reprogram the cells such as stem cells, multipotentant cells, and neuronal progenitor cells, by manipulating factors in the microenvironment.

In one embodiment the cells are administered in slurry with serum-free media to inhibit or delay proliferation and/or differentiation for some period of time of after implantation. In another embodiment, the number of cells in the composition are selected based on the desire to inhibit or reduce differentiation. In another embodiment the concentration of SAPNS is manipulated to control proliferation or differentiation. The concentration of SAPNS may also be selected to encourage or discourage the infiltration of host cells.

In another embodiment, the composition is used as a neuroprotective to minimize damage and scarring following neural injury. Peptide-based structures promote repair and regeneration of neural tissue (e.g., when self-assembling peptides are applied to a lesion in the brain as described in U.S. Patent Publication No. 2005/0287186 to Ellis-Behnke) The small size of the fibers within the scaffolds and/or the open "weave" structure of the materials permits extension of cell processes and allows adequate diffusion of nutrients and waste products in a manner that provides unique advantages for neural tissue regeneration.

In the course of promoting wound repair, the compositions may not only improve the final outcome (e.g., reduce scar formation resulting in an outcome that more closely resembles the original tissue), but also reduce the time required for healing. These results could not have been predicted on the basis of the results achieved following application to the injured central nervous system, given the substantial differences between neural and non-neural tissues.

IV. Methods of Administering Compositions

The compositions described herein, including, but not limited to, self-assembling materials (e.g., SAPs), cells, therapeutic and/or bioactive agents such as antibiotics and growth factors can be introduced into the peptide solution prior to, or after self-assembly of self-assembling materials into SAPNS in vitro or in vivo.

In a first embodiment, components of the composition are combined prior to administration. The cells and/or bioactive agents can be approximately evenly distributed throughout the scaffold or concentrated in one area or another (e.g., on or near the surface, within a core area, graded throughout the scaffold or a region thereof, or layered therein (e.g., concentrated in layers or evenly or unevenly distributed)). To achieve an approximately even distribution of the substance within the structure, one can mix the precursor-containing solution and the substance, which may also be in solution, prior to initiation of self-assembly.

The composition can be locally delivered at or near a target area in the body by injection (e.g., using a needle and syringe), or with a catheter, cannula, or by dispensing (e.g., pouring) from any suitably-sized vessel. The liquid formulations may be provided in a syringe or pipette having a barrel containing a composition including self-assembling peptides and cells and a means for expelling the composition from an open tip of the syringe or pipette (e.g., a plunger or bulb). The syringe may consist of one or more compartments (e.g., created by a divider running symmetrically or non-symmetrically along a long axis of the syringe barrel), so that mixing of the self-assembling peptides with cells and one or more other agents occurs at the time of application. In another embodiment, a first compartment may contain lyophilized self-assembling peptides or particles of self-assembling peptides, and a second compartment may contain a cell suspension in a solution, compatible with cell viability, that will also dissolve or hydrate the peptides and induce self-assembly prior to or during administration. The composition within the barrel can further include other components of the composition, such as serum, or any other bioactive agent described herein (e.g., one or more of a vasoconstrictor, a coloring agent, an anesthetic or analgesic agent, an antimicrobial (e.g., antibiotic, antiviral, or antifungal agent) or other therapeutic, collagen, an anti-inflammatory agent, a growth factor, or a nutrient). In yet another embodiment, the composition can be gelled and applied with an instrument, such as a spatula. The compositions can be delivered with the assistance of imaging guidance (e.g., stereotactic guidance) if necessary. Alternately, a material can be wetted with the composition and then used to apply a composition to an area of tissue.

The self-assembling material can be applied as a coating by spraying or dipping the device into the material, the material can be impregnated into a bandage, gauze or other absorbent material, the material can be mixed with a polymeric material. The material can also be formulated as a pharmaceutical foam. Pharmaceutical foams are pressurized dosage forms that, upon valve actuation, emit a fine dispersion of liquid and/or solid materials in a gaseous medium. In one embodiment, the foam contains the self-assembling material, in liquid or solid form, optionally in combination with one or more active agents. Suitable propellants include, but are not limited to, hydrofluoroalkanes (HFAs), such as 1,1,1,2-tetrafluoroethane (HFA 134a) and 1,1,1,2,3,3,3-heptafluoropropane (HFA 227), hydrocarbons, and carbon dioxide. Alternatively, the compositions can be applied as a gel. If desired, a small amount of ions (e.g., monovalent cations) can be added to a solution prior to application. This may speed the process of gel formation. Alternately, monovalent cations and cells can be applied after the solution has been administered.

The cells of the composition are administered after the self-assembling peptide. Following self-assembly, cells are distributed over the top of, or injected into, the SAPNS.

An endoscope can be used to deliver the compositions for treatment of a hollow organ (e.g., the esophagus, stomach, intestine, etc.) or body cavity (e.g., during minimally invasive surgery). Minimally invasive surgery refers to an approach to surgery whereby operations are performed with specialized instruments designed to be inserted through small incisions or natural body openings, often performed with endoscopic visualization. Examples include laparoscopic surgery, arthroscopic surgery, and endovascular surgery. An endoscope is typically a long, flexible tube-like device. In addition to allowing visualization of internal structures, many endoscopes have additional diagnostic (e.g. biopsy) and therapeutic capabilities (e.g. delivery of therapeutic agents) through special channels. Colonoscopes, sigmoidoscopes, bronchoscopes, cystoscopes, and laparoscopes, are variants of an endoscope having features making them particularly well suited for viewing certain organs, structures, or cavities. Any of these devices can be used to deliver the compositions.

As will be appreciated by those of ordinary skill in this art, the effective amount of a composition may vary depending on such factors as the desired biological endpoint, the composition to be delivered, the nature of the site to which the composition is delivered, and the nature of the condition for which the composition is administered. The amount of the composition provided can vary depending on the severity of the subject's condition. In general, the amount of the composition required will vary depending on various factors such as the size or extent of an injury (which can, in turn, be expressed in terms of the length of an incision, the caliber or number of damaged blood vessels, the degree of a burn, the size and depth of an ulcer, abrasion, or other injury). The amount may vary, for example, from a few microliters to several milliliters or more, e.g., tens or hundreds of milliliters. The number of cells administered will be determined by one skilled in the art based on the desired result (e.g. to induce differentiation or remain undifferentiated as described above) and the modulus of the tissue it is placed in. The interface between the tissue and material must match.

V. Kits

Exemplary kits include self-assembling peptides and one or more undifferentiated cells, precursor cells, progenitor cells, stem cells, and induced stem cells. The kits optionally include one or more of the following: bioactive agents, media, excipients and one or more of: a syringe, a needle, thread, gauze, a bandage, a disinfectant, an antibiotic, a local anesthetic, an analgesic agent, surgical thread, scissors, a scalpel, a sterile fluid, and a sterile vessel. The self-assembling peptides can be in solution or dry (e.g., as a dry powder). Components of the kit may be packaged individually and can be sterile. The kits are generally provided in a container, e.g., a plastic, cardboard, or metal container suitable for commercial sale. Any of the kits can include instructions for use.

In another embodiment, the self-assembling peptides can be dissolved in a suitable solvent (e.g., an aqueous medium such as sterile water, and stored for long periods of time prior to use). Peptide-containing solutions have been stored for up to two years without substantial loss of activity. If partial self-assembly occurs after a prolonged period of time, physical agitation (e.g., sonication) can be used to restore the material to a more liquid state prior to administration. Cells should be stored or shipped using a method consistent with viability such as in cooler containing dry ice so that cells are maintained below 4° C., and preferably below −20° C.

Kits containing syringes of various capacities or vessels with deformable sides (e.g., plastic vessels or plastic-sided vessels) that can be squeezed to force a liquid composition out of an orifice are provided. In one embodiment, the syringe or vessel contains multiple compartments, one containing cells in a solution compatible with cell viability and able to induce peptide self-assembly, and the other self-assembling peptides, which are mixed at the time of administration, through a common needle. Kits may be packaged including an endoscope and a vessel containing a solution comprising self-assembling peptides. Suitable endoscopes are known in the art and are widely available. Endoscopes are currently in use to deliver sclerosing agents to sites of esophageal bleeding.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

Example 1

SAPNS Delay Proliferation and Process Extension of PC12 Cells

Materials and Methods
Preparation of the SAPNS Solution

The SAPNS solution was prepared by mixing RADA16-I dry powder in an Eppendorf tube. The solution contained 5, 10, 20, or 30 mg of RADA16-I powder in 1 ml of Milli-Q water (Millipore), mixed, then sonicated for 30 sec and filtered; this produced 0.5, 1, 2, or 3% SAPNS. To assess purity, powder and liquid were combined and allowed to rest at room temperature for one month. An indication of its purity was that it remained clear and odorless.

PC12 Cell Culture

PC12 cells were purchased and plated in 10 cm polystyrene dishes, grown in a mixture of Hams F12k medium with 10% horse serum and 2.5% fetal bovine serum (FBS). Penicillin and streptomyosin was added along with 2 mM of L-glutamine and 1.5 g/l of sodium bicarbonate (Leach, et al., *J. Neural Eng.*, 4:26-34 (2007)). Cells were used after passage six. Cells were removed with trypsin-EDTA for transfer to the self-assembling nanofiber scaffold (SAPNS). The SAPNS was pre-buffered using the culture medium DMEM. The SAPNS at various concentrations was placed in separate wells and DMEM was added and changed in 1, 10 and 30 minute intervals. The phenol red in the culture medium was used as an indicator for a balanced pH condition. The cells were transferred to 0.5, 1, or 2% SAPNS and implanted into the material. On day 10 nerve growth factor (NGF) was added to assess the viability of the cell after the proliferation delay. Cells were incubated at 37° C. in 5% $CO_2$. Medium was changed every three days.

Results

In a 3-dimensional environment of SAPNS the cells appeared to become senescent, and in serum-free (SF) condition, did not divide for three days in 0.5% SAPNS concentration, or 5 days in 1% SAPNS. When the cells reached the boundary of the SAPNS they proliferated at the normal rate until they reached confluence and then stopped dividing. This process was repeated 3 times. Using 2% SAPNS concentration delayed proliferation of PC12 cells to day 7 in SF conditions. Care was taken during implantation of cells not to allow the culture medium to contact the cells during implantation in the culture. When NGF was added processes extended normally, but with a SAPNS concentration-dependant delay. This was repeated in serum conditions; proliferation was only delayed one day past the control in the 0.5% condition, however in the higher concentrations of 1% and 2%, division was observed at day 3 and 5, respectively. An increase in branching in the serum condition and an increase in branch size in the higher modulus material was also evident.

The control of proliferation in PC12 cells is cell-cell contact. When the cells grow to confluence they stop dividing. This appears to be the case when the cells are implanted into the SAPNS at different concentrations. This cell-cell mimic (SAPNS) controls the cell proliferation rate. The PC12 cells were able to grow normally after implantation in SAPNS. When NGF is added, normal transformation of the cells and neurite extension is observed. The higher the concentration of the SAPNS, the slower the neurite extension; the increase in density tends to have an increase in branches; and after adding NGF, the morphology of growth changes, depending on the modulus of the environment.

Example 2

SAPNS Concentration and Cell Density Effects Process Growth in Schwann Cells

Materials and Methods
Isolation and Culturing of Schwann Cells (SC)

The SCs were isolated as described by Morrissey, et al., *N. Neurosci.*, 11:2433-2442 (1991); Xu, et al., *J. Comp. Neurol.*, 351:145-160 (1995). Briefly, the sciatic nerves from adult green fluorescent protein-(GFP) transgenic Sprague-Dawley rats ["green rat CZ-004" SD TgN (act-EGFP) OsbCZ-004] were disassociated and placed in culture dishes with DMEM/F12 (Gibco) supplemented with 10% FBS (Gibco). When the outgrowth of migratory cells (predominantly fibroblasts) reached a near-confluent monolayer around the explants (about 7 days), the explants were transferred to new culture dishes with fresh medium. After three to five such passages (3-5 weeks) the cells that emerged from the explants were primarily SCs. The explants were then transferred to a 35-mm dish containing 1.25 µg/ml dispase, 0.05% collagenase, and 15% FBS in DMEM/F12 for incubation overnight at 37° C. in 5% CO2. On the following day the explants were dissociated and the cells were plated onto poly-1-lysine (0.01%; Sigma, St. Louis, Mo.)-coated dishes in DMEM/F12 with 10% FBS. Later the cultures were re-fed with the same medium supplemented with 20 µg/ml pituitary extract (Sigma) and 2 µM forskolin (Sigma) for dividing. When the SCs reached confluence they were rinsed in $Ca_2^+$- and $Mg_2^+$-free Hanks balanced salt solute ion (CMF-HBSS; Gibco) and briefly treated with 0.05% trypsin (Gibco) and 0.02% EDTA (Gibco) in CMF-HBSS. Cells were washed twice in DMEM/F12 with 10% FBS and transferred into new dishes at a density of $2\times10^6$ cells per 100-mm dish. When the cells reached confluence again they were collected for transplantation.

Results

At a concentration of 5,000 cells/µl, three days post implantation in 1% SAPNS in vitro, no processes were observed. After five days processes were observed extending from the cell body. When SCs were implanted in 2% SAPNS, process extension was not observed until 5 days post SAPNS implantation. Both conditions were in FBS. When the concentration of cells was increased to 10,000 cells/µl, process formation was delayed to 5 days in the 1% SAPNS concentration.

Example 3

The Concentration of SAPNS and the Presence of Serum Effects Process Development and Branching in Neural Precursor Cells (NPC)

Materials and Methods
Isolation and Culturing of Embryonic Neural Precursor Cells (NPC)

The generation and characterization of embryonic NPC cultures have been previously described (Enomoto, et al., *Eur. J. Neurosci.*, 17:1223-1232 (2003); Johe, et al., *Genes Dev.*, 10:3129-3140 (1996)). The hippocampi of embryonic day 16 (E16) embryos of GFP-transgenic Sprague-Dawley rats were dissected in cooled CMF-HBSS and dissociated mechanically. The cells were collected by centrifugation and re-suspended in DMEM/F12 supplemented with B27 supplement (2%, Gibco) N2 (1%, Gibco), epidermal growth factor (EGF, 20 ng/ml, Gibco), basic fibroblast growth factor (bFGF, 20 ng/ml, Sigma), penicillin (100 U/ml), and streptomycin (100 µg/ml). The cells were adjusted to $1\times10^5$ cells/ml and introduced into culture flasks. Half of the medium was replaced every 3 days. Typically the cells were mechanically dissociated approximately once each week and reseeded at approximately $1\times10^5$ cells/ml and then implanted into SAPNS of 1, 2 and 3% concentrations. Pictures were then taken at 5, 7, 9, 12, 15 and 34 days. This was repeated in a non-GFP expressing cell line and pictures were taken at 3, 5, 7, 9 days.

Results

Cells implanted in SAPNS at 1% concentration in SF conditions reached a maximum of 3±1 processes per cell by day 5 of culture. With serum added they reached a maximum of 9±1 processes per cell by day 7. Branching of the processes showed statistically significant differences. In SF conditions only 28% of the processes were branched by day 15 and the serum-added had 45% of the total processes branched (FIGS. 1 and 2).

Cells implanted in SAPNS at 2% concentration in SF conditions reached a maximum of 3±1 processes per cell, by day 9 of culture. With serum added, by day 9 it reached a maximum of 8±1 processes per cell. Branching of the processes showed statistically significant differences. In SF conditions only 35% of the processes were branched by day 15 and the serum-added had 58% of the total processes branched. If cells were plated in 2% it took longer, up to five to seven days before observing processes emerge. The processes continued to grow up to 30 days.

Cells implanted in SAPNS at 3% concentration in SF conditions reached a maximum of 3.5±1 processes per cell by day 15 of culture. With serum added cells reached a maximum of 11.5±1 processes per cell by day 12. Branching of the processes showed statistically significant differences. In SF conditions only 22% of the processes were branched by day 15; the serum added had 48% of the total processes branched by day 12.

All of the SF conditions have less than 4 processes per cell, while the conditions with FBS have greater than 6 processes by day 15. As the concentration of the material increases, the modulus of the material increases. As the modulus increases so does the number of processes per cell over time.

In all SF conditions the number of branched processes per cell remained below 1. The serum-added conditions after day 5 had more than one branched process per cell. As the concentration of the SAPNS increased there was an increase in the number of branches in the serum conditions. The maximum number of branched processes per cell reached was 5.5±1, in the serum-added condition 3% SAPNS condition at day 12 (FIG. 3). Note that in the 1% and 3% SF conditions the number of branched processes is less than one. However, in 2% it reaches one. In all serum-added conditions the branched processes are over 1 after day 5 in the 1% and 2% serum-added conditions, and after day 7 in the 3% condition.

Effects of SAPNS and Serum on Growth and Differentiation

There appears to be a concentration/modulus-dependant growth rate of the neural precursor cells when placed in culture. In the presence of serum, the higher the modulus, the more overall processes per cell. In serum-free conditions we do not see the modulus-dependant component in NPCs. The SAPNS appears to slow the growth rate and differentiation of the cells, thus allowing them to acclimate to the environment. This will be very important when the immune system tries attacking the cells when placed in vivo.

The NPCs appear to grow, or not grow, depending on the addition of the serum. With serum, the NPCs exhibit a concentration-dependant change in the response rate: the higher the concentration of SAPNS, the tighter the matrix. The ability of the serum to diffuse into the SAPNS shows a concentration-dependant response. In the 3% SAPNS concentration the number and the branch formation of the processes from the cells is delayed until day 9; in the 2% concentration the response is seen on day 7. In the lowest concentration the response is seen at day 5. All of this, of course, is dependent upon the volume of the SAPNS and the surface area of the bolus. When implanted in vivo this is much more pronounced, due to the limited ability of any material to diffuse across the implant boundary The higher the concentration of the SAPNS in vivo, the slower it will breakdown.

The fact that cells can survive in a serum-free (SF) condition is very beneficial because it provides much greater control over the medium chosen to grow the cells in vitro, before implanting them into a tissue. In culture, the branching rates of NPCs are lower in the SF conditions, signaling that the growth and differentiation of the cells is more controlled temporally.

Example 4

SAPNS Facilitates Gap Closer Following Brain Injury

Materials and Methods

In vivo applications to brain wounds were carried out by using 16 postnatal day 5 (P5) Syrian hamster pups, anesthetized with whole-body cooling. The scalp was opened, and the optic tract within the superior colliculus (SC) was completely severed with a deep knife wound through a slot cut in the cartilaginous skull, extending 1.5 mm below the surface, from the midline to a point beyond the lateral margin of SC (Ellis-Behnke, et al., *Proc. Nat. Acad. Sci. USA*, 103:5054-5059 (2006)). Animals were kept alive 30 days after surgery. During surgery, eight animals were treated by injection into the brain wound of 10 µl of 1% SAPNS. Control animals with the same lesions included 8 injected with 10 µl isotonic saline (Ellis-Behnke, et al., *Proc. Nat. Acad. Sci. USA*, 103:5054-5059 (2006)). Animals were sacrificed 30 day post lesion.

Results

In P5 hamsters, cells migrated into the 1% SAPNS implantation after transaction in the superior colliculus in 7 out of 8 cases. All control animals had cavities at one month survival in the location of the lesion, as evidenced by a large gap remaining at the site of the lesion. In animals treated with peptide scaffold, the gap was completely gone and tissue had reconnected across the injury site.

Example 5 pH Contributes to Growth and Differentiation of Cells in SAPNS Implants

Materials and Methods

Schwann Cells (SCs) in 3D Culture within the SAPNS

Before transplantation, the SCs, obtained from the sciatic nerves of GFP rats, were cultured within 1% SAPNS scaffold. Briefly, the SCs were collected and finally adjusted to $5\times10^5$ cells/µl. Then, 1 µl of the cell suspension was mixed with 9 µl of RADA16-I peptide; the mixture was gently and quickly plated to dish in DMEM/F12 with 10% FBS. The medium was changed at 1, 10, and 30 minutes after plating, and once every three days during the following days. The images of living cells were taken by two-photon confocal microscope (Zeiss LSM510 META, Jena, Germany).

Schwann Cells (SCs) Implantated into the Spinal Column

Thirty two adult Sprague-Dawley rats (220-250 g) were used in this project. The rats were divided into six groups: (1) SAPNS only, (2) uncultured SAPNS with SCs group 1, 4 and 8 weeks, (3) pre-cultured SAPNS-SCs alone group 2 and 8 weeks. Group one had two wild-type rats; groups two and three had six for each time point. Rats were anesthetized with ketamine (80 mg/kg) and xylazine (10 mg/kg). A dorsal laminectomy on the sixth and seventh cervical vertebrae was performed. The dura was incised longitudinally and pulled laterally. A spinal cord dorsal column transection was made between C6 and C7, followed by the removal of 1 mm dorsal column tissue. 10 µl of 1% SAPNS solution was injected into the lesion site or an equal volume of the cultured mixture of SAPNS and SCs, respectively, was transferred from the culture dish into the lesion cavity. After treatment the dura was closed. The muscle layers and skin were also closed with a suture. Manual bladder expression was performed twice daily until recovery of the bladder reflex.

Results

1% SAPNS implanted into the spinal cord alone eliminated the cysts when there was enough CSF and other ionic material left in the surgical site to buffer the material when implanted at the lesion site. This was repeated twice. Cells mixed with unbuffered 1% SAPNS and directly implanted showed apoptosis and necrosis (Guo, et al., *Nanomedicine*, 3:311-321 (2007)) as well as a reduced cyst formation at 4 and 8 weeks, compared with untreated controls. Pre-buffered 1% SAPNS with cells showed no cyst or cavity formation at 2 weeks or 8 weeks. Also, cells migrated into and out of the implantation site and were evident at up to a centimeter from the lesion site. There was good integrity and distinct lack of boundary.

There is also a pH contribution to the delay of the differentiation and growth of the cells. If the material is not buffered properly then there will be an acid shock; the cells that are in the implant of SAPNS will slowly disappear. This was shown in the spinal cord implant when the GFP SCs are mixed and implanted before they are buffered; the appearances of cysts are an indication of an acid shock. In the first implant of SAPNS at 1% concentration into a spinal cord without prebuffering, healing of the cord was evident. The injection of the pre-assembled material was made into a cavity that had a mixture of blood and CSF that allowed for immediate buffering of the SAPNS. During subsequent implantations of added cells and SAPNS, the lesion site was free of blood and CSF and therefore did not allow for sufficient buffering of the local environment. When the SAPNS was injected into the lesion site of the hamster the existing CSF was sufficient for immediate buffering of the material (see Example 4). SAPNS does not break down acidically, therefore no acid response (such as cells death over time) was observed.

We claim:

1. A composition for reducing or preventing proliferation or differentiation of multipotent, totipotent, or pluripotent cells in culture comprising
    viable human multipotent, totipotent, or pluripotent cells and a self-assembled nanofiber scaffold,
    wherein the nanofiber scaffold is formed from a solution of precursor peptides at a concentration of from 2% to 3% weight to volume,
    wherein the cells are at a concentration of 1,000 cells/µl to 100,000 cells/µl, and
    wherein the self-assembling peptide nanofiber scaffold contacts the cells to mimic cell-cell contact and prevent or reduce proliferation or differentiation of the cells for a period of between 1 and 30 days.

2. The composition of claim 1, wherein the cells comprise pluripotent stem cells, multipotent stem cells, progenitor stem cells, or a combination thereof.

3. The composition of claim 2, wherein the stem cells comprise adult stem cells, embryonic stem cells, or induced pluripotent cells.

4. The composition of claim 2, wherein stem cells can differentiate into neurocytes, cardiocytes, myocytes, chondrocytes, endothelial cells, osteocytes, or a combination thereof.

5. The composition of claim 4, wherein stem cells can differentiate into neurons, glial cells, astrocytes, or a combination thereof.

6. The composition of claim 1, wherein the self-assembling peptides are present in the non-cellular component of the composition at a concentration of about 3% weight to volume.

7. The composition of claim 1, wherein the self-assembling peptides comprise the amino acid sequence RADARADARADARADA (SEQ ID NO:1).

8. The composition of claim 1, wherein the self-assembling peptides comprise the amino acid sequence RAEARAEARAEARAEA (SEQ ID NO:2).

9. The composition of claim 1, wherein the nanofiber scaffold has a modulus of 0.01 to 1000 kPa.

10. The composition of claim 1, wherein the peptides are present at a concentration of greater than about 2% weight to volume.

11. The composition of claim 1, wherein the nanofiber scaffold has a modulus of 0.01 to 10 kPa.

12. The composition of claim 1, wherein the self-assembling peptides are present in the non-cellular component of the composition at a concentration of 2% wt/vol.

13. The composition of claim 1, wherein the composition is maintained in the absence of serum.

14. The composition of claim 1, wherein the composition is maintained in the absence of serum and growth factors.

15. The composition of claim 1, wherein properties of the self-assembling peptide nanofiber scaffold that reduce proliferation or differentiation of the cells comprise the concentration of the self-assembling peptide nanofiber scaffold, the pH of the self-assembling peptide nanofiber scaffold, the modulus of the self-assembling peptide nanofiber scaffold, and the absence of serum.

16. A method for inhibiting cell differentiation or proliferation comprising contacting multipotent, totipotent, or pluripotent cells with the self-assembling peptide nanofiber scaffold of claim 1.

17. The method of claim 16, wherein the self-assembling peptides are present at a concentration of about 3% wt/vol.

18. The method of claim 16, wherein cell proliferation or differentiation is delayed for at least 1 to 30 days compared to a control.

19. The method of claim 16, wherein the cells comprise pluripotent stem cells, multipotent stem cells, progenitor stem cells, or a combination thereof.

20. The method of claim 19, wherein the stem cells comprise adult stem cells, embryonic stem cells, or induced pluripotent cells.

21. The method of claim 19, wherein stem cells can differentiate into neurons, glial cells, astrocytes, or a combination thereof.

22. The method of claim 16, wherein the self-assembling peptides comprise the amino acid sequence RADARADARADARADA (SEQ ID NO:1).

\* \* \* \* \*

SEQUENCE LISTING

```
<160> NUMBER OF SEQ ID NOS: 3

<210> SEQ ID NO 1
<211> LENGTH: 16
<212> TYPE: PRT
<213> ORGANISM: Artificial Sequence
<220> FEATURE:
<223> OTHER INFORMATION: Synthetic construct

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic Construct

<400> SEQUENCE: 2

Arg Ala Glu Ala Arg Ala Glu Ala Arg Ala Glu Ala Arg Ala Glu Ala
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct

<400> SEQUENCE: 3

Arg Ala Arg Ala Arg Ala Arg Ala Asp Ala Asp Ala Asp Ala Asp Ala
1               5                   10                  15
```